(12) United States Patent
Sharma et al.

(10) Patent No.: US 8,993,831 B2
(45) Date of Patent: Mar. 31, 2015

(54) FOAM AND DELIVERY SYSTEM FOR TREATMENT OF POSTPARTUM HEMORRHAGE

(75) Inventors: Upma Sharma, Somerville, MA (US); Irina Gitlin, Brookline, MA (US); Parisa Zamiri, Brookline, MA (US); Toby Freyman, Waltham, MA (US); Rany Busold, Medford, MA (US); Lee Core, Needham, MA (US); Janet Chie Komatsu, Cambridge, MA (US); Jennifer Mortensen, Somerville, MA (US)

(73) Assignee: Arsenal Medical, Inc., Watertown, MA (US)

( * ) Notice: Subject to any disclaimer, the term of this patent is extended or adjusted under 35 U.S.C. 154(b) by 0 days.

(21) Appl. No.: 13/536,557

(22) Filed: Jun. 28, 2012

(65) Prior Publication Data

US 2013/0110066 A1    May 2, 2013

Related U.S. Application Data

(60) Provisional application No. 61/554,181, filed on Nov. 1, 2011.

(51) Int. Cl.
*A61F 13/53* (2006.01)
*A61K 47/34* (2006.01)
*A61P 7/04* (2006.01)
(Continued)

(52) U.S. Cl.
CPC ......... *A61L 24/0036* (2013.01); *A61L 24/0015* (2013.01); *A61L 24/046* (2013.01); *A61L 27/14* (2013.01); *A61L 27/56* (2013.01); *A61L 31/04* (2013.01); *A61L 31/146* (2013.01); *A61L 2300/418* (2013.01); *A61L 2400/04* (2013.01); *A61L 2430/22* (2013.01)
USPC .......................... 604/369; 424/400; 514/772.3

(58) Field of Classification Search
CPC .......... A61F 13/53; A61K 47/34; A61K 9/00; A61P 7/04
USPC .......................................................... 604/369
See application file for complete search history.

(56) References Cited

U.S. PATENT DOCUMENTS

| 4,764,377 A | 8/1988 | Goodson |
| 5,364,627 A | 11/1994 | Song |

(Continued)

FOREIGN PATENT DOCUMENTS

| WO | WO-94/18956 A1 | 9/1994 |
| WO | WO-03/020161 A2 | 3/2003 |

(Continued)

OTHER PUBLICATIONS

Merriam-Webster's Collegiate Dictionary. 11th Edition: 2004.*

(Continued)

*Primary Examiner* — Tatyana Zalukaeva
*Assistant Examiner* — Sara Sass
(74) *Attorney, Agent, or Firm* — Kacvinsky Daisak Bluni PLLC

(57) ABSTRACT

Medical implants and methods useful in treating postpartum hemorrhage are disclosed. The implants, in some embodiments, comprise polyurethane foams having advantageous mechanical and other properties selected to promote hemostasis when brought in contact with an inner wall of a uterus. Methods of making and deploying such implants are also disclosed.

10 Claims, 17 Drawing Sheets

(51) Int. Cl.

| | | |
|---|---|---|
| *A61K 9/00* | (2006.01) | |
| *A61L 24/00* | (2006.01) | |
| *A61L 24/04* | (2006.01) | |
| *A61L 27/14* | (2006.01) | |
| *A61L 27/56* | (2006.01) | |
| *A61L 31/04* | (2006.01) | |
| *A61L 31/14* | (2006.01) | |

(56) References Cited

U.S. PATENT DOCUMENTS

| | | | |
|---|---|---|---|
| 5,538,735 | A | 7/1996 | Ahn |
| 5,567,612 | A | 10/1996 | Vacanti et al. |
| 5,569,528 | A | 10/1996 | Van der Loo et al. |
| 5,725,568 | A | 3/1998 | Hastings |
| 5,800,476 | A | 9/1998 | Piunti |
| 5,842,477 | A | 12/1998 | Naughton et al. |
| 5,922,340 | A | 7/1999 | Berde et al. |
| 5,944,341 | A | 8/1999 | Kimura et al. |
| 5,980,927 | A | 11/1999 | Nelson et al. |
| 6,002,968 | A * | 12/1999 | Edwards ................... 607/101 |
| 6,086,911 | A | 7/2000 | Godbey |
| 6,214,370 | B1 | 4/2001 | Nelson et al. |
| 6,382,526 | B1 | 5/2002 | Reneker et al. |
| 6,495,124 | B1 | 12/2002 | Samour |
| 6,520,425 | B1 | 2/2003 | Reneker |
| 6,524,608 | B2 | 2/2003 | Ottoboni et al. |
| 6,596,296 | B1 | 7/2003 | Nelson et al. |
| 6,655,366 | B2 | 12/2003 | Sakai |
| 6,676,953 | B2 | 1/2004 | Hexamer |
| 6,676,960 | B2 | 1/2004 | Saito et al. |
| 6,685,956 | B2 | 2/2004 | Chu et al. |
| 6,685,957 | B1 | 2/2004 | Bezemer et al. |
| 6,689,374 | B2 | 2/2004 | Chu et al. |
| 6,695,992 | B2 | 2/2004 | Reneker |
| 6,712,610 | B2 | 3/2004 | Abdennour et al. |
| 6,716,449 | B2 | 4/2004 | Oshlack et al. |
| 6,737,447 | B1 | 5/2004 | Smith et al. |
| 6,753,454 | B1 | 6/2004 | Smith et al. |
| 6,821,479 | B1 | 11/2004 | Smith et al. |
| 6,855,366 | B2 | 2/2005 | Smith et al. |
| 6,858,222 | B2 | 2/2005 | Nelson et al. |
| 6,861,142 | B1 | 3/2005 | Wilkie et al. |
| 6,861,570 | B1 | 3/2005 | Flick |
| 6,913,760 | B2 | 7/2005 | Carr et al. |
| 7,029,495 | B2 | 4/2006 | Stinson |
| 7,033,603 | B2 | 4/2006 | Nelson et al. |
| 7,033,605 | B2 | 4/2006 | Wong |
| 7,048,913 | B2 | 5/2006 | Hexamer |
| 7,048,946 | B1 | 5/2006 | Wong et al. |
| 7,074,392 | B1 | 7/2006 | Friedman et al. |
| 7,135,194 | B2 | 11/2006 | Birnbaum |
| 7,172,765 | B2 | 2/2007 | Chu et al. |
| 7,198,794 | B1 | 4/2007 | Riley |
| 7,214,506 | B2 | 5/2007 | Tatsumi et al. |
| 7,235,295 | B2 | 6/2007 | Laurencin et al. |
| 7,285,266 | B2 | 10/2007 | Vournakis et al. |
| 7,309,498 | B2 | 12/2007 | Belenkaya et al. |
| 7,323,190 | B2 | 1/2008 | Chu et al. |
| 7,462,362 | B2 | 12/2008 | Kepka et al. |
| 7,678,366 | B2 | 3/2010 | Friedman et al. |
| 7,737,060 | B2 | 6/2010 | Strickler et al. |
| 7,765,647 | B2 | 8/2010 | Smith et al. |
| 7,799,965 | B2 | 9/2010 | Patel et al. |
| 7,803,395 | B2 | 9/2010 | Datta et al. |
| 7,824,699 | B2 | 11/2010 | Ralph et al. |
| 7,959,616 | B2 | 6/2011 | Choi et al. |
| 7,959,848 | B2 | 6/2011 | Reneker et al. |
| 7,959,904 | B2 | 6/2011 | Repka |
| 7,997,054 | B2 | 8/2011 | Bertsch et al. |
| 2001/0021873 | A1 | 9/2001 | Stinson |
| 2002/0176893 | A1 | 11/2002 | Wironen et al. |
| 2003/0017208 | A1 | 1/2003 | Ignatious et al. |
| 2003/0068353 | A1 | 4/2003 | Chen et al. |
| 2003/0171773 | A1 | 9/2003 | Carrison |
| 2003/0195611 | A1 | 10/2003 | Greenhalgh et al. |
| 2004/0030377 | A1 | 2/2004 | Dubson et al. |
| 2004/0076661 | A1 | 4/2004 | Chu et al. |
| 2005/0033163 | A1 | 2/2005 | Duchon et al. |
| 2005/0042293 | A1 | 2/2005 | Jackson et al. |
| 2005/0106211 | A1 | 5/2005 | Nelson et al. |
| 2005/0276841 | A1 | 12/2005 | Davis et al. |
| 2006/0153815 | A1 | 7/2006 | Seyda et al. |
| 2006/0276831 | A1 | 12/2006 | Porter et al. |
| 2006/0293743 | A1 | 12/2006 | Andersen et al. |
| 2007/0087027 | A1 | 4/2007 | Greenhalgh et al. |
| 2007/0155273 | A1 | 7/2007 | Chu et al. |
| 2007/0176333 | A1 | 8/2007 | Greene et al. |
| 2007/0232169 | A1 | 10/2007 | Strickler et al. |
| 2007/0293297 | A1 | 12/2007 | Schugar |
| 2008/0053891 | A1 | 3/2008 | Koops et al. |
| 2008/0132936 | A1 | 6/2008 | Sawhney et al. |
| 2008/0245371 | A1 * | 10/2008 | Gruber .................... 128/831 |
| 2008/0264423 | A1 * | 10/2008 | Duchon et al. ............ 128/830 |
| 2008/0269126 | A1 * | 10/2008 | Ballance et al. ............ 514/12 |
| 2008/0281350 | A1 | 11/2008 | Sepetka et al. |
| 2009/0155326 | A1 | 6/2009 | Mack et al. |
| 2010/0249913 | A1 | 9/2010 | Datta et al. |
| 2010/0291182 | A1 | 11/2010 | Palasis et al. |
| 2010/0318108 | A1 | 12/2010 | Datta et al. |
| 2011/0184530 | A1 | 7/2011 | Datta et al. |
| 2011/0237994 | A1 | 9/2011 | Russ et al. |
| 2012/0107439 | A1 | 5/2012 | Sharma et al. |

FOREIGN PATENT DOCUMENTS

| | | |
|---|---|---|
| WO | WO-2007/052042 A2 | 5/2007 |
| WO | WO-2008/013713 A2 | 1/2008 |
| WO | WO 2011/007352 | 1/2011 |

OTHER PUBLICATIONS

Rhee et al, "Treatment of type II endoleaks with a novel polyurethane thrombogenic foam; Induction of endoleak thrombosis and elimination of intra-aneurysmal pressure in the canine model" *Journal of Vascular Studies*, 42:2, 321-328, Aug. 2005.

Kanani et al., "Review on Electrospul Nanofibers Scaffold and Biomedical Applications", Trends Biomater, Artif, Organs, vol. 24(2), pp. 93-115, (Aug. 2010).

Biomedical Structures, Glossary: Common Biomedical Textile Terms (accessed Oct. 12, 2011), 1-11 pgs.

Bini, T.B. et al., "Electrospun poly(L-lactide-co-glycolide) biodegradable polymer nanofiber tubes for peripheral nerve regeneration", Nanotechnology, 15, 2004, 1459-1464.

Jose, Moncy V. et al., "Fabrication and characterization of aligned nanofibrous FLGA/Collagen blends as bone tissue scaffolds", Polymer, 50, 2009, 3778-3785.

Liao, Yiliang et al., "Preparation, characterization, and encapsulation/release studies of a composite nanofiber mat electrospun from an emulsion containing poly(lactic-co-glycolic acid)", Polymer, 49, 2008, 5294-5299.

Wei, Kai et al., "Emulsion Electrospinning of a Collegen-like Protein/PLGA Fibrous Scaffold: Empirical Modeling and Preliminary Release Assessment of Encapsulated Protein", Macromolecular Bioscience, 11, 2011, 1526-1536.

Sy, Jay C. et al., "Emulsion as a Menas of Controlling Electrospinning of Polymers", Advanced Materials, 21, 2009, 1814-1819.

International Search Report mailed Jan. 18, 2011 for International Application No. PCT/US2010/057010 (3pgs).

International Search Report mailed Jan. 5, 2012 for International Application No. PCT/US2011/47615 (3 pgs).

International Search Report mailed Jan. 2, 2013 for International Application No. PCT/US2012/062732.

International Search Report mailed Jun. 18, 2013 for International Application No. PCT/US2013/046281 (4 pgs).

* cited by examiner

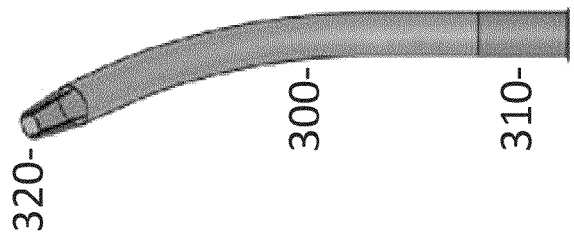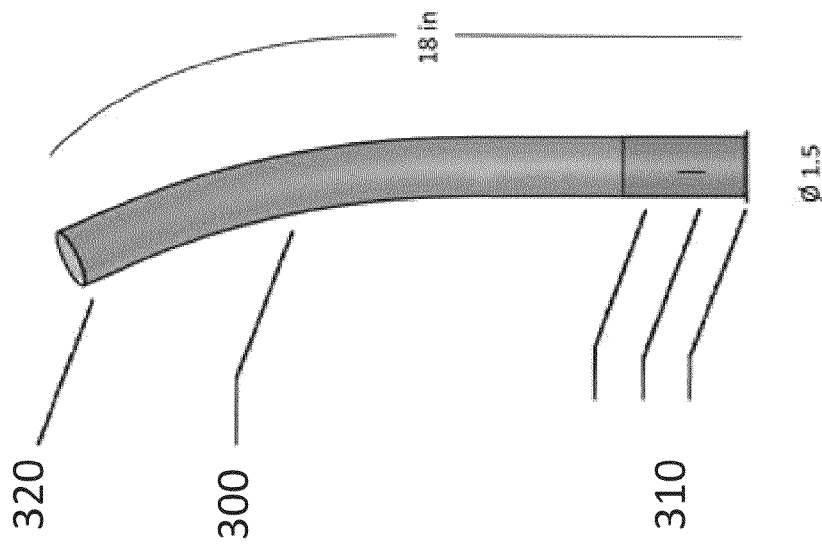
Figure 16

US 8,993,831 B2

FOAM AND DELIVERY SYSTEM FOR TREATMENT OF POSTPARTUM HEMORRHAGE

CROSS-REFERENCE TO RELATED APPLICATIONS

This application claims priority to U.S. Provisional Application Ser. No. 61/554,181 filed Nov. 1, 2011, which is incorporated by reference for all purposes.

TECHNICAL FIELD

The present invention relates to implants and methods for treatment of postpartum hemorrhage.

BACKGROUND

This application relates to, and incorporates by reference the entire disclosure of, U.S. patent application Ser. No. 12/862,362.

Each year, roughly 14 million women worldwide suffer from postpartum hemorrhage, defined as blood loss exceeding 500 mL, making it one of the most common causes of morbidity and mortality following childbirth. Severe postpartum hemorrhage, involving blood loss in excess of 1000 mL, occurs in approximately 3% of all vaginal deliveries and a large number of caesarean deliveries. See e.g. Janice M. Anderson and Duncan Etches, *Prevention and Management of Postpartum Hemorrhage*, 75 μm. Family Physician 875-882 (Mar. 15, 2007). Complications may include infection, hypotension, anemia, fatigue, hemorrhagic shock and ultimately death. Id. There were, according to World Health Organization statistics, approximately 132,000 deaths worldwide due to postpartum hemorrhage in 2011 and, accordingly, there is an ongoing need for treatments that rapidly and effectively stanch uterine bleeding.

Common causes of postpartum hemorrhage include uterine atony, coagulopathy, retention of placental tissue, and genital tract trauma. Different treatments may be indicated for each of these causes—for example, uterine massage may be indicated for postpartum hemorrhage due to uterine atony, while closure of lacerations may be indicated for hemorrhage due to trauma—and the process of identifying a cause and selecting a suitable treatment therefore adds complexity and potentially delays the delivery of treatment. Moreover, in developing or rural environments, the availability of treatments for postpartum hemorrhage across the spectrum of causes may be limited. Accordingly, a need exists for systems and methods for treating postpartum hemorrhage that can be rapidly deployed and are useful in treating the condition across the full spectrum of its causes.

BRIEF DESCRIPTION OF THE INVENTION

The invention addresses the needs described above by providing, in one aspect, a uterine implant and delivery system for the treatment of hemorrhage including a pre-formed collapsible and/or expandable foam body that can be positioned within a uterus. In certain embodiments, the implant optionally includes one or more features including a hollow center, a membrane enveloping the foam implant, one or more pull strings for removal of the foam implant, and a drug for delivery to the uterus. In certain embodiments, the implant is removed after use by collapsing it and passing it through the lower genital tract, and in certain embodiments the implant is degraded, resorbed or otherwise decomposed by normal physiological mechanisms or by the application of an exogenous agent.

In another aspect, the invention is a formulation or formulations that react to form a uterine implant when delivered to a uterus and a delivery system for delivering such formulations to a uterus. The delivery system optionally forms an implant that is enveloped by a membrane during its formation and/or its residence in a body.

In another aspect, the invention is a method of treating uterine hemorrhage. In certain embodiments, the method includes contacting a uterine wall with an implant comprising a biocompatible polymer foam. The implant may include multiple foam bodies which optionally have an edge portion and a thicker central portion. The polymer foam can have a compression force deflection value at 50% compression of less than 100 kPa, or it can apply a pressure of at least 30 mmHg to the uterine wall. The implant can, in various embodiments, have a volume of between 100% and 200% of the postpartum human uterus, and/or it can include one or more porous membranes or a drug that promotes blood clotting. The method may also include applying an agent to dissolve at least part of the implant following use. The implant may cause uterine contractions by applying pressure to the uterine wall, and the foam may be formed within the uterus of the patient or may be pre-formed. In other embodiments, the method includes positioning a uterine implant that includes at least one biocompatible foam polymer body and one or more membranes disposed over the exterior surface of the implant within the uterus of a patient. In various embodiments, the implant may include multiple foam bodies which optionally have an edge portion and a thicker central portion. The polymer foam can have a compression force deflection value at 50% compression of less than 100 kPa, or it can apply a pressure of at least 30 mmHg to the uterine wall. The method may also include removing the implant by applying tension to the first end of the porous membrane.

DESCRIPTION OF THE DRAWINGS

The figures provided herein are not necessarily drawn to scale, with emphasis being placed on illustration of the principles of the invention.

FIG. 16 includes a photo illustration of delivery devices according to embodiments of the invention.

DETAILED DESCRIPTION

Figure 1:
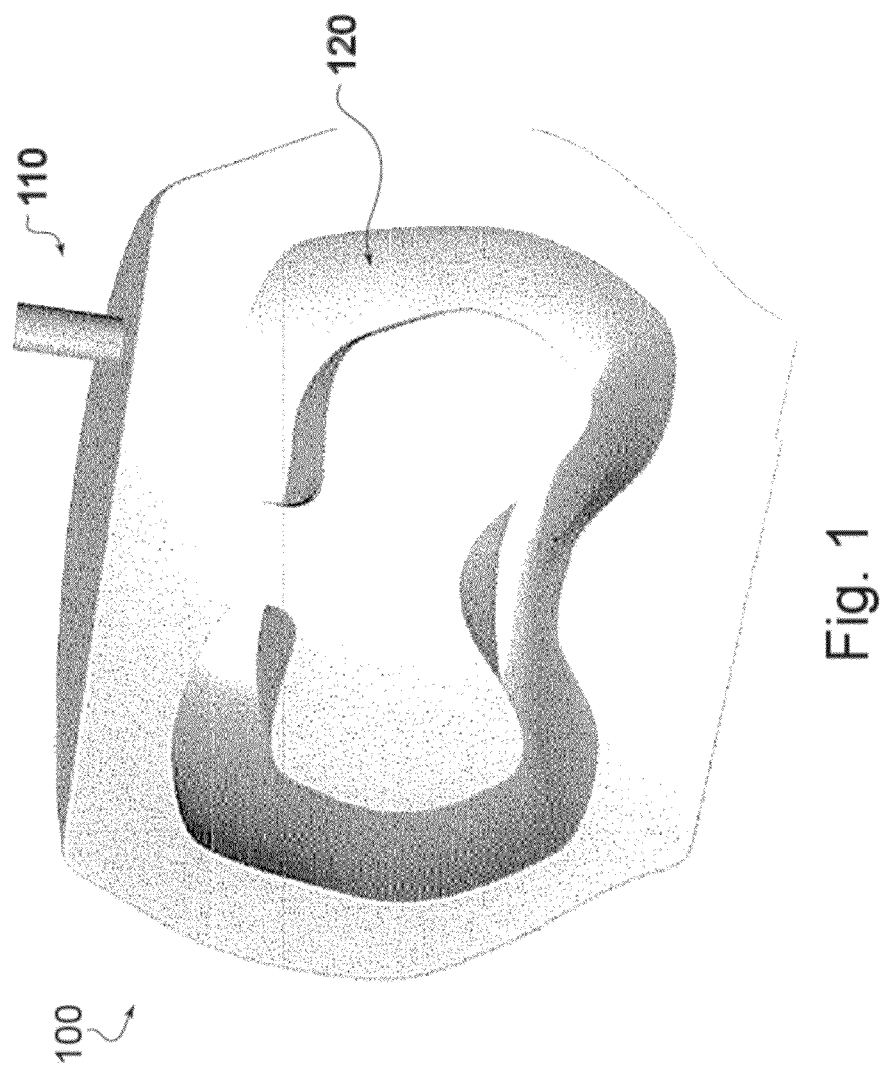
FIG. 1 includes a schematic drawing of a mold for making implants according to certain embodiments of the invention.

The invention includes a polyurethane foam implant and a delivery applicator. The polyurethane foam implant is compliant, with compression force deflection ("CFD") values at 50% compression preferably below 100 kPa, and more preferably less than 10 kPa. The elastic properties of the foam allow it to expand from a compressed state and conform to a site or sites of hemorrhage on the uterine wall which may be irregular or may have a variety of challenging morphologies. Foam implants of the invention are preferably hydrophobic, to help prevent absorption of water or blood while deployed. Foams used in implants of the invention can be closed-cell or open-cell. Foam implants of the invention preferably have recovery values between 80% and 100% and are made from bulk materials having high tensile strength so that foams of the invention can withstand the application of forces by, for example, pulling during removal from a uterus, as discussed below. Additionally, foam implants of the invention are highly compliant, allowing them to expand to up to 50-100% or more of the volume of the uterus without inducing uterine rupture. Foams of the implant can also be resorbable, as discussed below.

The Foam:

The foam comprising the implant is, in preferred embodiments, biocompatible and, in certain embodiments, resilient or viscoelastic. In preferred embodiments, the foam implant can be removed from the body via a simple removal mechanism (similar to removal of a tampon), and does not induce adhesions. In some embodiments, the foam is at least partially resorbable, degradable or decomposable and/or at least partially ensheathed by a membrane as is discussed in more detail below.

Foams of the invention are preferably made of polyurethane, but can be of any suitable composition, including without limitation polyolefins (e.g. polyethylene, polypropylene, ethylene vinyl acetate copolymer, etc.), natural and synthetic latex, silicone, fluoropolymer (e.g. PTFE, etc.), polystyrene, epoxy, poly(vinyl chloride) (PVC), or phenolic polymers. Polyolefin foams, polystyrene, epoxy, PVC and phenolic foams can be flexible, but are generally more rigid than polyurethane foams, which may affect certain characteristics such as compression force deflection, and accordingly may affect their performance in achieving homeostasis via the mechanisms discussed in more detail below. Polyolefin foams can be made by any suitable means, including without limitation expansion with a gaseous blowing agent dispersed into a polymer melt, leaching of a condensed phase in the polymer matrix, or sintering small resin particles together under heat and pressure. Latex foams can also be made by any suitable means, including without limitation whipping precursors with air then heating, vulcanizing and curing.

Although not wishing to be bound to any theory, the inventors believe that implants of the invention stop hemorrhage via three independent yet synergistic mechanisms: form morphology, tamponading and induction of uterine contraction.

With respect to foam morphology, the foam's pore structure, including size, morphology and tortuosity, can permit blood to enter the foam but resist blood flow. In cases of severe hemorrhage, a high flow rate or high blood velocity is thought to interfere with normal clotting by diluting activated clotting factors and disrupting fibrin clots before they have a chance to build. In addition, a large clot is required to close a large injury, and the time required for formation of a large clot is greater than for a small clot. By contrast, in smaller injuries, clotting is thought to occur more efficiently because the concentration of activated clotting factors is rapidly built up and sustained, and because the fibrin clots are able to grow rapidly to a size and strength sufficient to seal a small breach in a vessel wall. In certain embodiments, implants of the invention absorb hemorrhaged blood into small pores through which blood flows slowly and at relatively higher pressures, facilitating normal clotting and accelerating hemostasis. The foam also provides a large surface area for platelet and cell attachment and activation, and for initiation of the coagulation cascade. In preferred embodiments, the foam has an open-cell structure with a pore size of 0.01 to 1 mm, and a high surface-to-volume ratio, though the invention is also compatible with closed-cell structures. Without wishing to be bound to theory, low mass density foams with high pore densities are thought to be particularly well suited to slow rates of blood flow and to concentrate clotting factors, thereby promoting faster clotting. Foams having both open- and closed-cell morphologies are compatible with the invention.

In certain embodiments, the foam includes polyurethanes or other polymers that promote clotting, as is discussed in more detail below. The use of polymers that improve or promote clotting may synergize with the effects of the morphology of the foam, and other factors discussed below, resulting in more efficient or faster clotting.

In certain embodiments, the properties of the polyurethane used to make the foam are tailored to improve thrombogenicity, as discussed in U.S. patent application Ser. No. 12/862,362, which is incorporated by reference as discussed above. In certain some embodiments, the foam includes a pro-coagulant to promote clotting at the site of injury. Pro-coagulants useful in the invention include, without limitation, glucosamine-based materials, cellulose, collagen, gelatin, fibrinogen, thrombin, fibrin, biologics, synthetic hemostatic peptides such as RADA, freeze-dried platelets, freeze-dried plasma, gelatin, silica particles, kaolin, glass beads, anti-fibrinolytic drugs and zeolites. Useful glucosamine-based materials include, without limitation, chitin, chitosan, and poly-N-acetyl glucosamine. Useful biologics include, without limitation, factor VII, factor XII, factor XI, factor VIII, factor IX or other coagulation factors from human or animal sources. Anti-fibrinolytic drugs including, without limitation, tranexamic acid and aminocaproic acid are used in certain embodiments of the invention. Some embodiments of the invention include vasoconstrictors such as epinephrine, norepinephrine, amphetamines, vasopressin, phenylephrine, pseudoephedrine, psilocybin and the like to induce constriction of major blood vessels.

In some embodiments, the foam includes silver nitrate (AgNO$_3$), which promotes clotting through a cautery action and has an antimicrobial effect.

Exogenous agents such as antibiotics, pro-coagulants or AgNO$_3$ can be incorporated throughout foams by adding them to bulk formulations used to make pre-formed or in-situ forming foam implants. Agents can also be applied to the outer surface of pre-formed foams and/or to the surfaces of membranes enveloping or partially enveloping foam implants of the invention by any suitable means known in the art.

In some embodiments, after the implant is deployed, portions of the foam that are in contact with blood preferentially absorb water from blood, decreasing the solvent concentration and thereby increasing the concentration of activated clotting factors, accelerating hemostasis. The foam matrix—the walls separating the pores—optionally provides cell separation between cells and serum, and preferentially absorbs water or permits water to flow through the walls of pores, further concentrating clotting factors at the foam surface and contributing to hemostasis.

In some embodiments, the implant includes a heating or cooling element, or a chemical mixture that undergoes a strongly exothermic or endothermic reaction upon deployment of the implant, for example (without limitation) silver nitrate. When a foam wall of the implant contacts the inner wall of the uterus, sealing of blood vessels is accelerated by a cautery effect or a cryocautery effect caused by the heating or cooling of the implant.

In some embodiments, the expanded foam can selectively bind injured and bleeding tissues in which basement membranes have become exposed. Injured tissues can be characterized by the presence of basement membrane proteins that are not usually accessible in non-injured tissues and include, without limitation, laminin, fibronectin, collagens type I and IV, fibroblast growth factors, damaged matrix proteins or peptides that are not exposed in uninjured tissue (e.g. tertiary collagen), and intracellular proteins that become exposed when cells are ruptured. Injured tissues can also be characterized by the presence of proteins related to clotting, including factor VIII. The foam in these embodiments includes molecules capable of selectively binding the proteins listed above, or similar proteins as known in the art. Such molecules include, without limitation, peptides, proteins, carbohydrates, and RNA aptamers, all of which are covalently linked to the prepolymer used to make the foam via amine or thiol groups or other reactive or functionalizable groups.

Another mechanism of action of implants of the invention is a tamponading effect on the uterus: in certain embodiments the foam expands to apply pressure to the uterine wall, compressing blood vessels, reducing blood flow and promoting clotting via the mechanisms discussed above. The foam implants preferably apply sufficient pressure to close small vessels held open by blood pressure. As a non-limiting example, in a patient with physiologically normal diastolic blood pressure, 80 mmHg, an implant of the invention, when deployed, can apply more than 80 mmHg (or approximately 1.5 PSI) of pressure to the uterine wall, promoting closure of open arterial blood vessels. The inventors have found that the application of lower pressures, for example of 40 mmHg, also achieve significant (80% or more) reductions in flow. Implants that apply tamponading pressure preferably, though not necessarily, include hydrophobic foam, to permit the application of pressure to the uterine wall while advantageously resisting the absorption of blood. To the extent that non-absorbed blood accumulates in the uterine space, the additional volume of blood adds to the pressure exerted by the implant on the uterine wall, enhancing the tamponading effect and reducing hemorrhage.

Another mechanism of action of implants of the invention is induction of uterine contraction: in certain embodiments, when the foam expands to apply pressure to the uterine wall, as discussed above, it stretches myometrial smooth muscle fibers within the uterine wall, stimulating contraction. As the smooth muscle fibers contract, the diameter of small uterine vessels is reduced, thereby reducing blood flow and promoting clotting as discussed above. Certain embodiments of the invention advantageously compress in response to normal uterine contraction forces, minimizing patient discomfort. In certain embodiments, compression is aided by forming the implant so that it has one or more void spaces, and/or forming the implant from a foam having a low CFD. If patient discomfort is too great, the implant can simply be removed and replaced with a smaller implant or an implant that applies less compressive force to the uterine wall, for example an implant comprising a foam having a lower CFD value. In certain embodiments, the invention includes a drug to induce uterine contraction, preferably one of oxytocin and misoprostol.

Because they can induce uterine contraction, embodiments of the invention can be useful in treating postpartum hemorrhage due to uterine atony. Embodiments of the invention may also be useful in treating postpartum hemorrhage due to coagulopathy, as the reduction of flow, high clotting surface area, and other aspects of the invention improve the conditions for clotting in cases where a patient has a clotting deficit. Implants of the invention can also be advantageous in treating postpartum hemorrhage in patients with abnormal uterine anatomy, such as uterine fibroids and uterine septum, as the induction of uterine contraction facilitates the establishment of conformal contact between the implant and the uterine wall.

Infection is a potential complication of postpartum hemorrhage. In certain embodiments of the invention the risk of infection is reduced by incorporating AgNO$_3$ and/or one or more anti-bacterial agents into the foam. As discussed above, the anti-bacterial agent is deposited on the surface of the foam implant after it is formed, incorporated into the bulk of the foam during formation, and/or incorporated into the membrane enveloping the foam. The anti-bacterial agent is optionally released from the foam and/or the membrane and delivered to the patient. Anti-bacterial agents useful with the invention include, without limitation, silver nitrate, silver sulfadiazine, gentamycin, penicillin, tetracycline, oxytetracycline, metacycline, doxycycline, minocycline, fradiomycin sulfate, erythromycin, and chloramphenicol.

In preferred embodiments, foam implants of the invention are pre-formed around a specially designed mold 100 as shown in FIG. 1. The foam is created through a two-part chemical reaction involving mixing a polyol and an isocyanate. Polyols that are useful in the invention include, without limitation, ethylene glycol, diethylene glycol, 1,4 butanediol, trimethylolopropane, poly(ethylene glycol) (PEG), polypropylene glycol) (PPG), PEG-PPG random and block copolymers, poly(lactic acid) (PLA), poly(glycolic acid) (PGA), PLGA, poly(caprolactone) (PCL), and various block copolymer of PEG/PPG and PLGA, PCL and their copolymers. Isocyanates that are used in the invention include, without limitation, diphenyl methane diisocyanate, toluene diisocyanate, and hexamethylene diisocyanate. The polyurethane foam is preferably formed according to the methods described in U.S. patent application Ser. No. 12/382,362. Implants of the invention, whether solid or comprising hollow portions, can be made by any suitable means known in the art, including without limitation machining and molding. After forming, hollow portions can be created by coring out portions of the formed foam using any suitable means known in the art. Alternatively, hollow foam implants may be made by molding: the polyol and isocyanate phases can be mixed and poured over the mold and allowed to foam. The mold consists of a chamber 120 and an air inlet/outlet 110. Following molding, the foam is optionally further processed to shape it, or to treat the surface, for example by removing the outer layer which may have an undesirable pore structure due to contact with the mold. These techniques will be known to those skilled in the art. As discussed below, pull strings are optionally incorporated into the foam during forming or in post-processing.

The Implant:

The uterus typically resembles an inverted pear: the superior portion of the uterine cavity is relatively wide, while the inferior portion including the cervix is narrowed and slightly elongated. In the postpartum phase, the uterus has an irregular internal contour and can be variable in shape (long and narrow, or short and wide) but it generally retains its inverted pear-shaped proportions. The size of the postpartum uterus can vary from 5 to 13 cm in the antero-posterior direction, 14-25 cm in length and 7-14 cm in width (See, e.g. Mimi C. Berman and Harris L. Cohen, 1997, *Diagnostic Medical Sonography: Obstetrics and Gynecology* (1997)). The effective internal volume of the postpartum uterus is estimated at between 250 and 1,000 mL, based on fluid volumes reported in studies of Rusch balloon treatment for postpartum hemorrhage. See e.g. R. Keriakos and A. Mukhopadhyay, *The use of the Rusch balloon for management of severe postpartum haemorrhage*, 26 J. Obstetrics and Gynaecology 335-338 (May 2006). In preferred embodiments, implants of the invention are sized to be slightly larger than the uterine volume. Preferably, the implant is oversized to the uterus by between 1% and 300%; more preferably, the implant is oversized between 7.5% and 150%. Oversizing the implant contributes to its ability to conformally contact the irregular uterine wall and apply pressure to induce uterine contraction and tamponading effect. The ability to conformally contact the uterine wall, whether due to oversizing, high compliance, or other factors, advantageously permits treatment of patients with abnormal uterine anatomy, including without limitation patients with uterine fibroids or a uterine septum.

Figure 2:
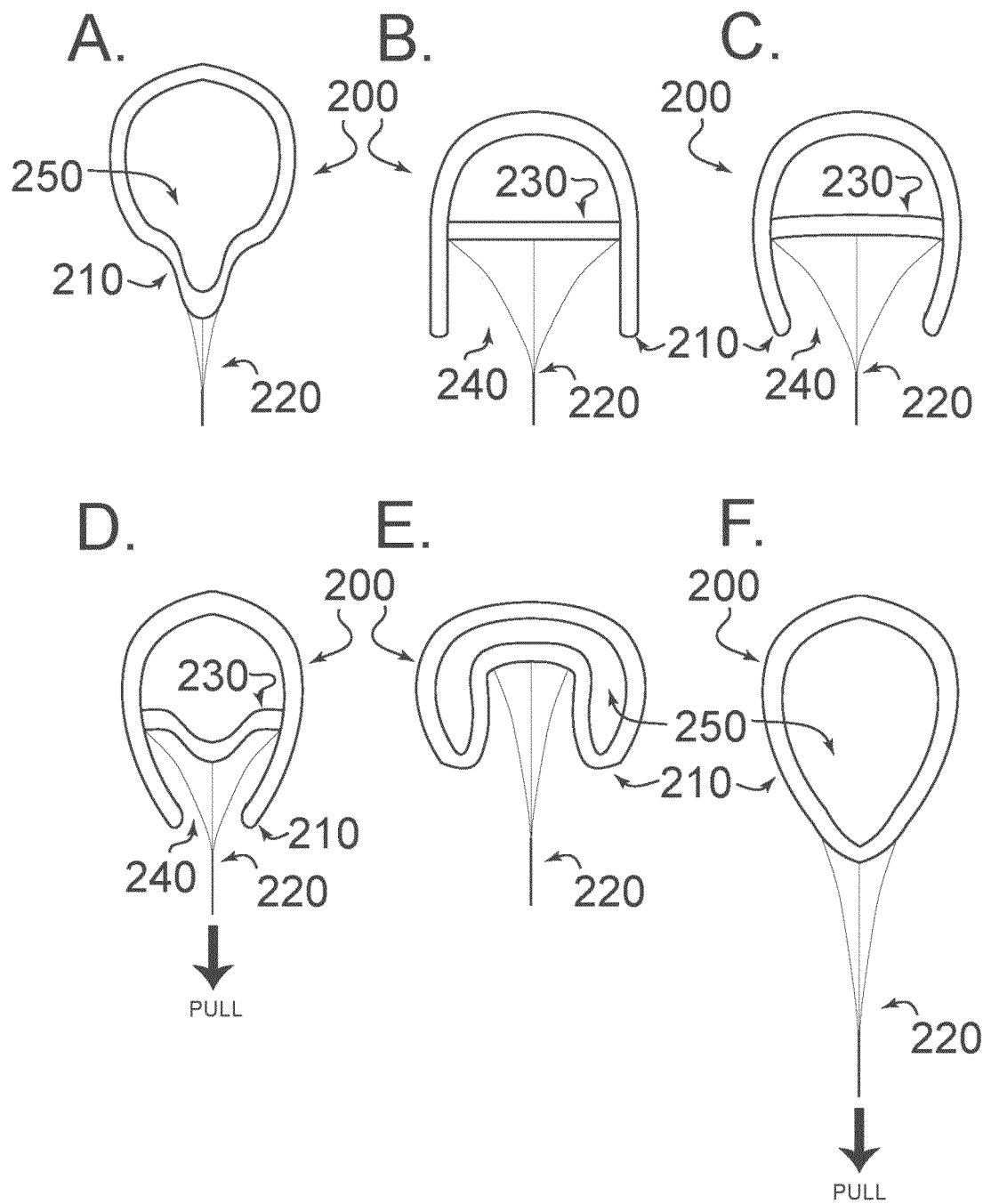
FIG. 2 includes a series of cross-sections of different implant designs according to embodiments of the invention.

With respect to the embodiments of FIGS. 2 and 4-6, implants of the invention are shaped to fit within a postpartum uterus, so in certain embodiments they have the same inverted pear proportions as a postpartum uterus. As shown in FIG. 2, the implant 200 has a foam wall 210 preferably having a thickness of 0.2 to 7 cm, and more preferably 0.5 to 3 cm. This thickness range is preferred because foams of this thickness have sufficient volume to absorb blood and promote clotting, and to provide the outward force necessary to induce uterine contraction and tamponading, but remain easily collapsible to facilitate delivery and removal through the cervix, as discussed below.

In the embodiment of FIG. 2A, the implant 200 includes a foam wall 210 shaped to resemble the inner surface of the uterus. In the embodiments depicted in FIG. 2, the implant has a hollow center 250; in some embodiments, the implant includes multiple recesses within the foam body, or includes an opening 240, preferably in the inferior aspect as shown in FIGS. 2B-D. The implant 200 also includes, in some embodiments, at least one pull string 220 that hangs below the implant and, preferably, through the cervix and lower genital tract so that the ends of pull string 220 are accessible outside of the body. Although three pull strings 220 are depicted in FIG. 2, any suitable number of pull strings can be used in implants of the invention. The pull strings 220 are secured to or within the foam wall 210 by any suitable means known in the art, including threading, molding or suturing the pull strings 220 through the foam wall in its expanded state, or encapsulating the strings within the foam wall 210 during foam formation.

Hollow implants of the invention can include expandable braided structures to provide support, promote full expansion, and facilitate removal. Braided structures compatible with the invention include, without limitation, braided wires or fibers comprising shape memory materials as discussed above, In one example, an expandable braided structure is deployed separately and into the hollow cavity of the foam following foam deployment. The braid can self-expand or be manually expanded to improve foam contact with the uterine wall, then collapsed along with the foam implant to facilitate its removal.

In certain embodiments, such as those depicted in FIG. 2B-D, the implant includes a reinforcing member 230 such as a strut or struts, which provides support against compression. The reinforcing member 230 is formed of the same material as the foam wall 210, or is formed of any suitable material, including without limitation metal or plastic. Suitable metals include, without limitation, stainless steel, spring tempered stainless steel, MP35N, and Nitinol, while suitable plastics include ultra-high molecular weight polyethylene, PEEK, PTFE and similar materials. A stiffer foam formulation than the foam wall 210 may also be used for the reinforcing member 230. In certain embodiments, the foam wall 210 is constructed around a collapsible, umbrella-like structure made up of Nitinol, which provides strength to the foam wall to facilitate contact and the application of pressure to the uterine wall. Removal of implants in these embodiments is achieved by collapsing the umbrella-like structure, thereby reducing the cross-sectional area of the implant and facilitating removal through the lower genital tract. The use of Nitinol in these embodiments also promotes expansion of the implant during deployment: because Nitinol has shape memory, the implant can be compressed within an applicator as discussed below, then returned to a pre-set shape when deployed.

In contrast to the embodiment of FIG. 2A, in which foam wall 210 forms a closed body, the embodiments of FIG. 2B-D have an open end 240, preferably the inferior end. In these embodiments, the pull-strings 220 may be attached to a flexible reinforcing member 230. The implant 200 is manufactured, as shown in FIG. 2B, so that when the foam wall 210 is unconstrained, reinforcing member 230 is fully extended, and opening 240 is at its maximum. When there is no external pressure on implant 200, it preferably adopts its cast shape. When the implant 200 is deployed in a uterus, the foam wall 210 contacts the uterine wall, the reinforcing member 230 is compressed, and the opening constricts. Because the pull strings 220 are attached to reinforcing member 230 in these embodiments, pulling on the pull strings 220 bends the reinforcing member 230, collapsing the wall 210 of the implant 200 and closing the opening 240 to facilitate separation of the implant 200 from the uterine wall and removal through the lower genital tract. Alternatively, any implant of the invention can be removed surgically using any suitable technique.

In another embodiment, shown in FIG. 2E-F, when the implant 200 is deployed, a portion of the foam wall 210 is folded in on itself. The folded portion of the foam wall 210 reinforces the unfolded portion of the foam wall 210, facilitating contact with the uterine wall and the application of pressure thereto. When pull strings 220 are pulled, the folded portion of the foam wall 210 connected to the pull strings 220 moves in the direction of tension, unfolding the implant 200 and facilitating its compression and removal through the lower genital tract.

Figure 9:
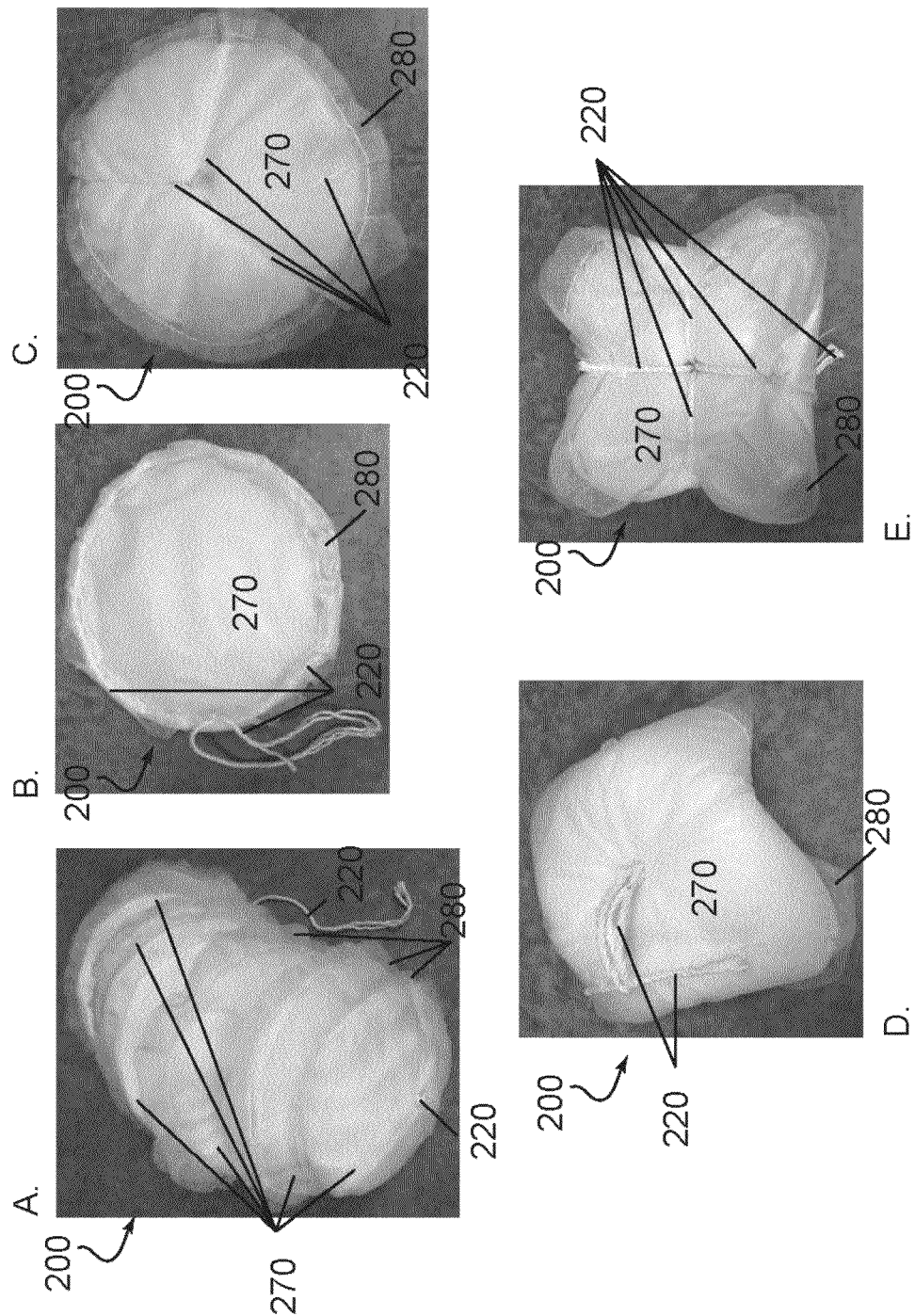
FIG. 9 includes a series of photo illustrations of implants of the invention comprising one or more foam disks.

In some embodiments, such as the one shown in FIG. 9, the implant 200 includes one or more foam disks 270. The disks are optionally connected to or bound to one another, for example via a common thread such as a pull string 220 as shown in FIG. 9A, or by enclosing them within a common membrane as discussed below. When the implant 200 is deployed, multiple disks 270 are advantageously able to move relative to one another within the uterus so as to conform to the irregular shape of the uterine wall. In preferred embodiments, the disks are not perfectly symmetrical, but are, for example, thicker in the middle and thinner at the edges: being thicker in the middle permits the disks 270 to more efficiently fill the volume of the uterus along a long axis of the implant, while the thinner edges permit the implant 200 to achieve conformal contact with the uterine wall, which may be irregularly shaped in some patients. The disks 270 can have any useful shape and incorporate flat or curved surfaces or both. In some embodiments, the implant 200 can include disks 270 of different sizes, shapes or compositions. Multiple disks 270 of the implant 200 can be inserted sequentially rather than all at once, so that a physician or other caregiver can advantageously tailor the number and/or size of disks used to the size and shape of the patient's uterus and/or the patient's degree of bleeding.

In preferred embodiments, disks 270 are thinner at the edges than in the center, permitting efficient space-filling and, simultaneously, conformal contact with the uterine wall as discussed above. In some embodiments, the disks 270 have a first generally flat surface a convex or conical surface opposite the flat surface such that, when stacked, the disks 270 do not simply form an even structure with a relatively small volume, but instead arrange irregularly relative to one-another. When positioned in a uterus, disks 270 having such a structure may advantageously achieve conformal contact with irregular areas of the uterine wall, while symmetrical and even disks may not. In some embodiments, disks of multiple diameters, thicknesses and/or shapes may be used.

Any suitable arrangement of pull strings 220 can be used to collapse implants 200 comprising one or more disks 270. As shown in FIG. 9B, the disk 270 can be encircled by a pull string 220 in a purse-string arrangement, whereby the application of tension to the free ends of the pull string 220 results in the application of circumferential compressive force to the disk 270, decreasing the amount of space occupied by the implant 200 and facilitating its passage through a constricted space such as a cervix or the lower genital tract. In other embodiments shown in FIGS. 9A and C-E, a pull string may pass through the center of the disk or disks. With respect to the embodiments depicted in FIGS. 9D and E, which represent two views of the same implant 200 comprising a disk 270 and a membrane 280 (discussed in more detail below), a plurality of pull strings 220 are secured to the membrane 280 and/or the disk 270 at individual points about the circumference of the disk 270. When tension is applied to the strings, the anchor points of the pull strings 220 are drawn toward the point where the pull strings 220 pass through the disk, compressing the disk 270 and facilitating its passage through a constricted space, such as a cervix or the lower genital tract.

In some embodiments, such as those shown in FIG. 11B, the implant 200 includes a plurality of small foam spheres 271, which are optionally tethered to a common pull string 220. As non-limiting examples, the small foam spheres 271 can be tethered to a single pull string 220 running approximately through the center of each sphere 271 like a string of pearls, as shown in the figure, or the pull string 220 can be threaded off center through one or more of the spheres 271. The spheres 271 can be provided in a form that permits a user to thread any selected number of spheres 271 onto one or more common pull strings 220 in any selected manner so as to tailor the number and arrangement of spheres to the needs of the patient. In some embodiments, the implant 200 can include spheres having different sizes and/or compositions. Implants of the invention that include multiple spheres, it is believed, can advantageously move around the uterus to conform to its shape and efficiently In some embodiments, the implant 200 includes one or more foam ropes 272. Ropes can be of any useful form, including without limitation woven or flat, and may be of any chosen length and other dimensions. Implants 200 comprising ropes 272 may be cut to an appropriate size prior to implantation to tailor the implant's dimensions to each patient. Implants 200 comprising one or more ropes 272 also preferably comprise a highly compressible foam formulation to permit tight packing within a uterus or other structure.

Figure 10:
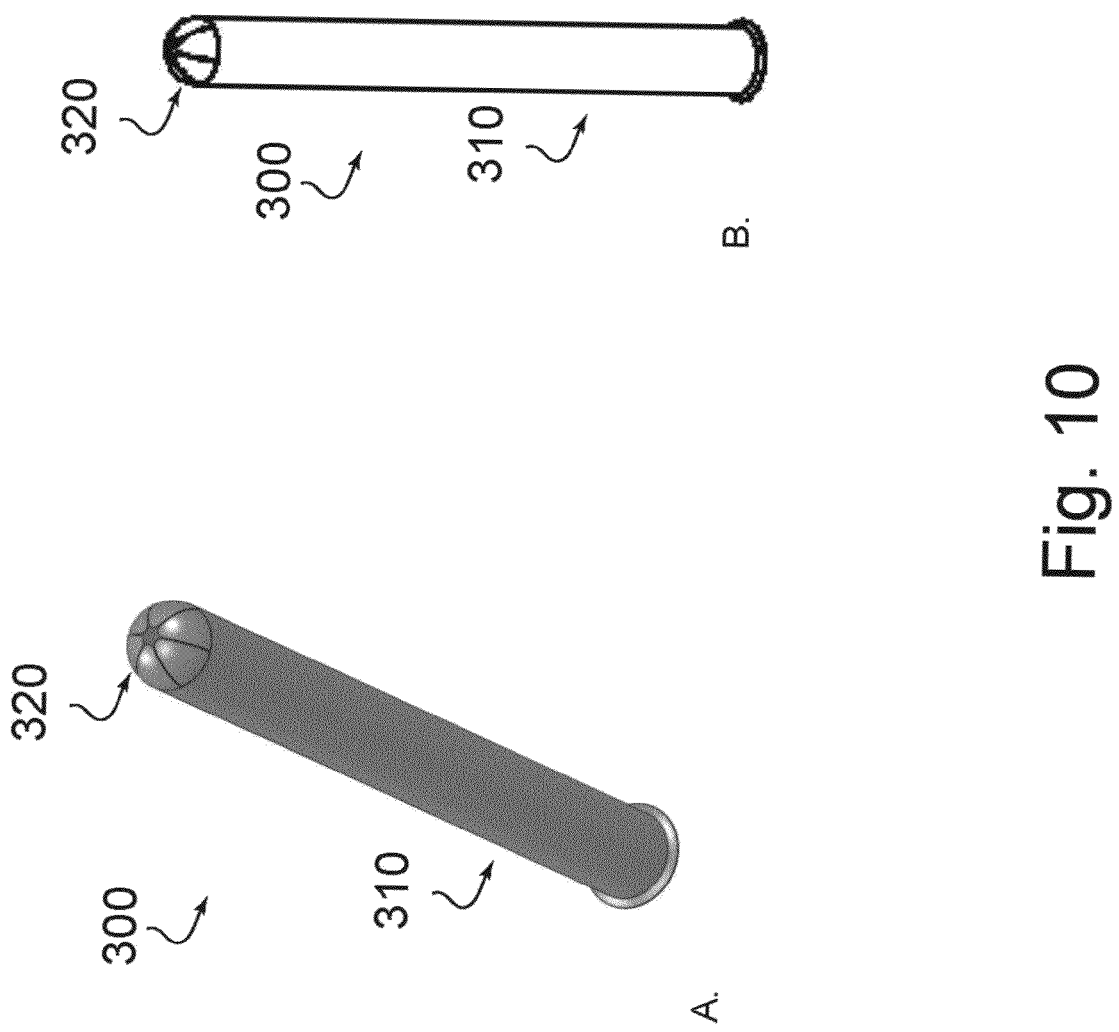
FIG. 10 includes a depiction of an applicator for a preformed foam implant according to certain embodiments of the invention.
Figure 11:
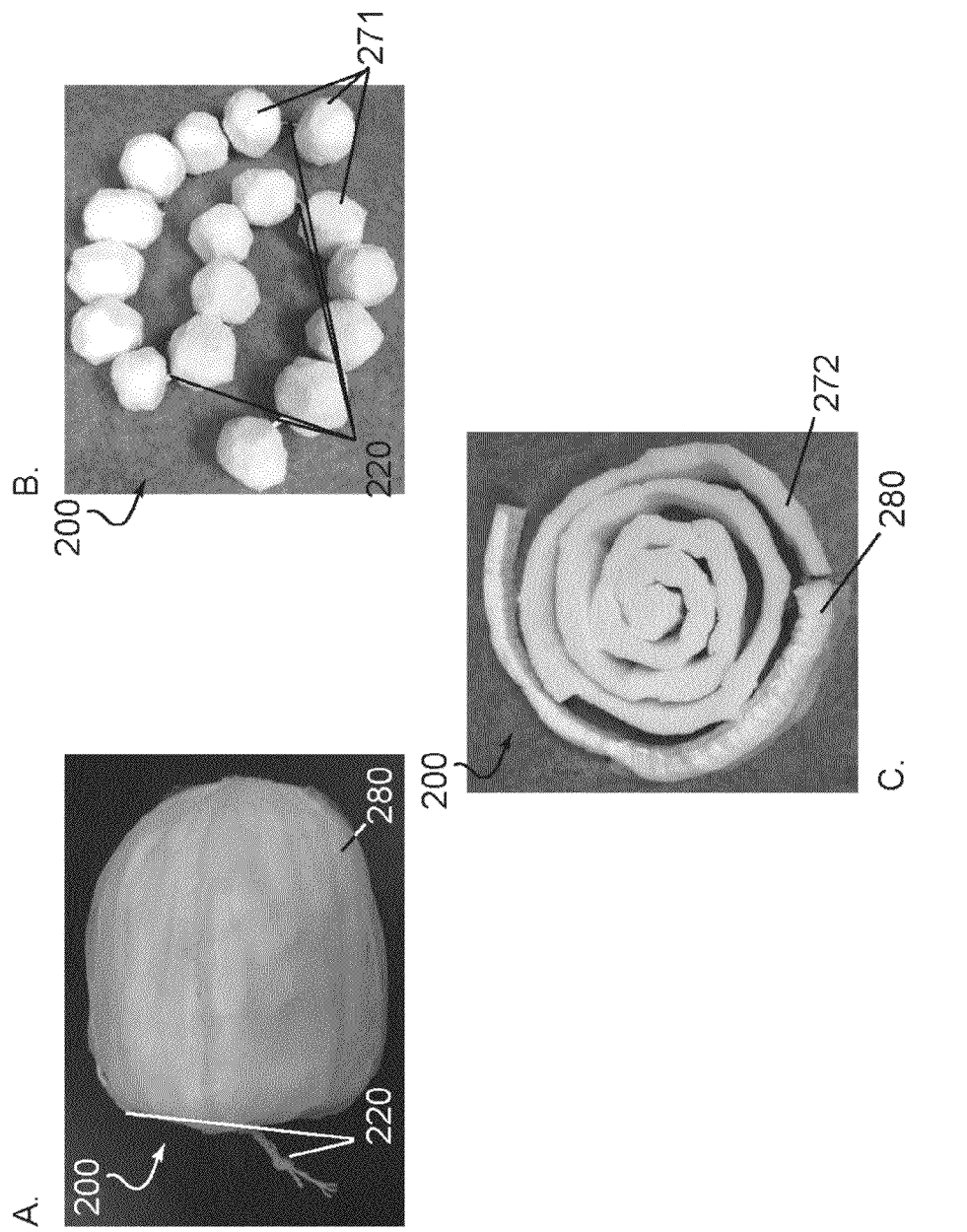
FIG. 11 includes a series of photo illustrations of implants according to certain embodiments of the invention.

In some embodiments, such as those shown in FIGS. 9-11, implants of the invention are at least partially enveloped by a thin membrane 280 to separate the foam surface from the uterine wall. Membrane 280 is preferably biocompatible and optionally biodegradable or bioresorbable. Membrane 280 may be composed of any suitable material, including without limitation nylon, and may be porous or non-porous, and permeable, semi-permeable, or non-permeable. The membrane can be non-adherent, or can include non-adherent regions or layers. For example, the membrane may include polytetrafluoroethylene (PTFE) or expanded PTFE (ePTFE). In some embodiments, a PTFE or ePTFE coating is applied to a surface of the membrane that will contact the uterine wall. The inner and outer surfaces of the membrane 280 may be textured or smooth, and may be sized to loosely envelop the fully-expanded implant, or to fit snugly around the fully or partially-expanded implant.

Membrane 280 may be folded or layered, and may include multiple layers of the same or a similar material, or layers of different materials. Folds or layers are optionally secured to one-another to limit their movement relative to one another and to ease implant removal or adjustment. Any suitable means for securing membrane folds or layers to one another may be used, including without limitation stitching, gluing, melting, melt pressing, solvent bonding, etc. In some embodiments, layers or folds of the membrane 280 are separate and free to move relative to one-another. In membranes 280 that include layers or folds, it is preferred for at least one layer to be lubricious or otherwise characterized by low friction. Individual layers of membrane 280 may have distinct structural features, such as perforations or pleats, to tailor the physical characteristics of the membrane 280 and the implant 200.

In some embodiments, membrane 280 is a nylon fabric. Membrane 280 may incorporate one or more pull strings 220. Pull strings may be anchored directly to the membrane 280 or to both the foam implant 200 and the membrane 280, in which case the membrane 280 will possess sufficient strength and/or flexibility to withstand the application of force without tearing or deforming to an extent that inhibits implant removal.

In implants comprising multiple disks, spheres, or other substructures, each substructure may be covered by a separate membrane 280, and/or a single membrane 280 may encompass the entire implant 200. Similarly, each substructure may have a separate pull string 220, and the plurality of pull strings can be braided or otherwise secured to one-another to facilitate withdrawal and prevent tangling. Pull strings are optionally secured to implants 200 or to the membrane 280 by inserting them directly through the material, or through the use of securement features such as hooks, rings, sutures, staples, or any other suitable mechanism.

Figure 12:
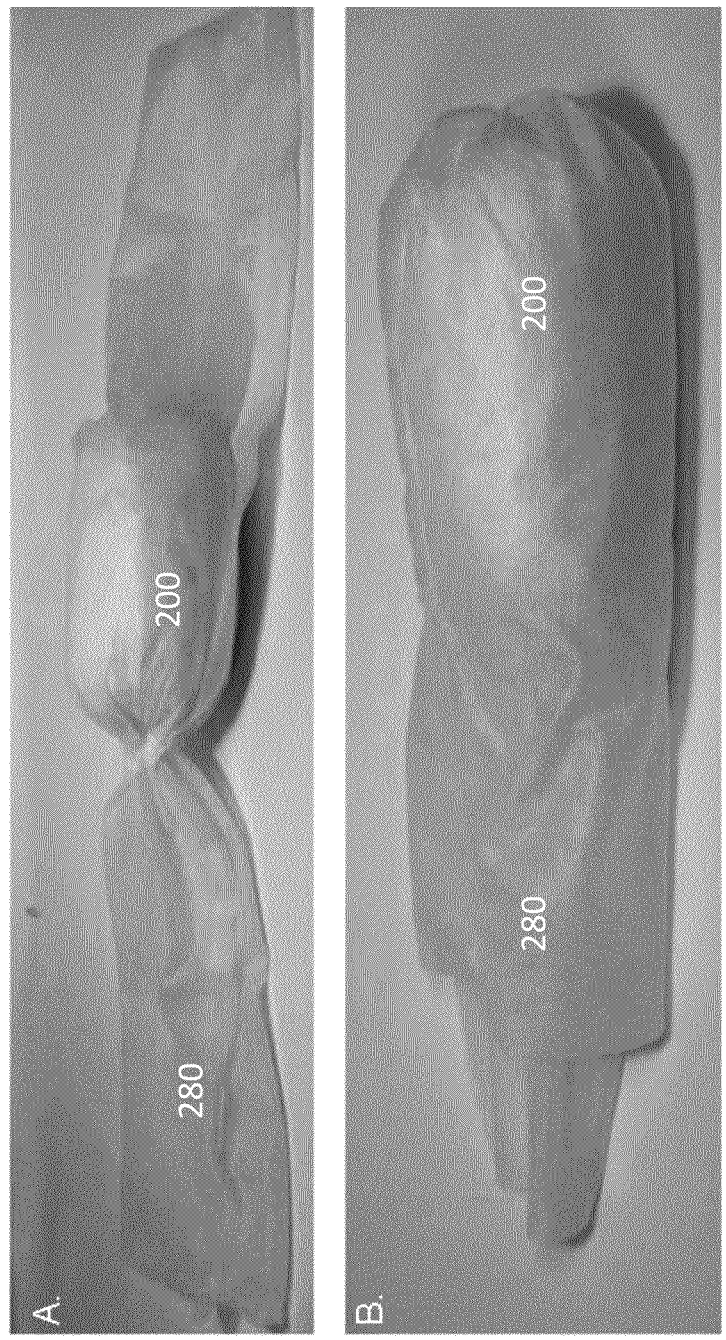
FIG. 12 includes a series of photo illustrations of implants according to certain embodiments of the invention.
Figure 13:
FIG. 13 includes a photo illustration of a portion of an implant according to certain embodiments of the invention.

In certain embodiments, the implant 200 is withdrawn from a patient by applying tension to the membrane 280 directly, which encompasses or is secured to the implant 200. In a preferred embodiment, the implant 200 is at least partially enveloped in a tubular or bag-shaped membrane 280, as is shown in FIG. 12. In a preferred embodiment, membrane 280 has a roughly tubular form which is cinched in the middle, forming first and second bag-like structures ("bags") that are attached end-to-end. The implant is positioned within the first bag adjacent to the cinch point (FIG. 12A), then the second bag is drawn over the top of the implant and the first bag, such that the implant 200 is covered by both bags. When in use, the implant is preferably positioned within a uterus so that the ends of both the first and second bags extend from the uterus into the lower genital tract and outside the body. After use, the implant may be withdrawn by applying tension to the portion of the first bag that extends into the lower genital tract and/or outside the body. In this procedure, the second bag remains substantially in place until after passage of all of the disks through the lower genital tract and out of the body. The outer surface of the membrane 280 preferably has low friction or is lubricious, or a lubricant is added to the surface of membrane 280 between the first and second bag-like structures, permitting the implant 200 and the first bag to slide easily against the second bag during removal, and advantageously protecting the uterine wall from shear and frictional forces. Alternatively, the membrane 280 can incorporate a lubricating polyethylene layer or sheet, as is shown in FIG. 13. In preferred embodiments, this lubricating layer is perforated, efficiently providing low friction while minimizing weight and bulk. Examples of other low friction materials suitable for incorporation into the membrane 280 include, without limitation, PTFE, FEP, ePTFE, PE, PP and other polymers. Suitable lubricious coatings that can be applied to the membrane 280 include, without limitation, MDX silicone, or a water-soluble lubricant such as K-Y® Jelly (McNeil-PPC, Morris Plains, N.J.).

Figure 14:
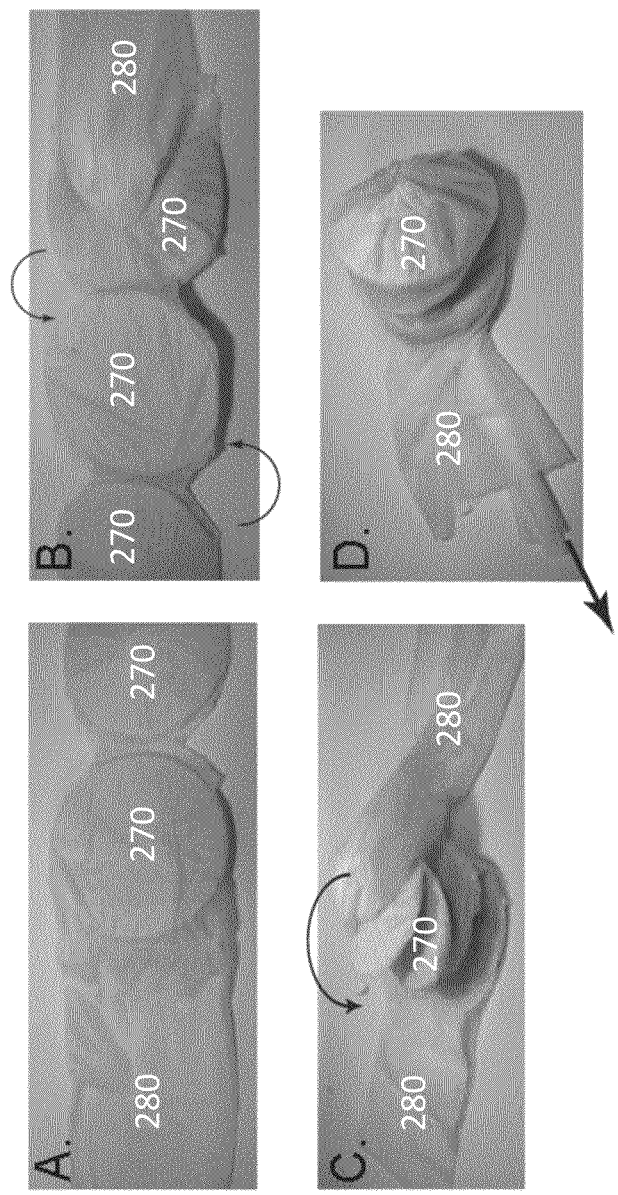
FIG. 14 includes a photo illustration of portions of implants according to certain embodiments of the invention.

In some embodiments, such as that shown in FIG. 14, an implant 200 comprising a plurality of disks 270 utilizes a membrane 280 disposed in a bag-like design similar to that described above: The disks 270, each of which optionally has a flat face and a convex or conical face opposite the flat face or is otherwise asymmetrical as discussed above, are placed in a line, optionally alternating face up and face down. The membrane 280 is then wrapped around the line of disks and secured to itself (e.g. sewn together, melted, heat-bonded, glued, tacked, etc.) to form a sleeve, which is then closed at one end, preferably near one of the disks 270, to form a first bag. The membrane 280 may be secured to bring its ends together to form the sleeve or bag, and additional tacks or seams are optionally placed about each disk to limit the movement of the disks 270 relative to one-another and to the membrane 280, as shown in FIGS. 14A and B. In preferred embodiments, an open end of the first bag extends beyond the last of the disks 270, while a second bag is attached to the closed end of the first bag, as shown in FIGS. 15B and C. The disks 270 are then stacked on one-another, as shown in FIG. 14C, and the second bag is drawn over the outside of the disks 270 and the first sleeve, resulting in the arrangement shown in FIG. 14D. The implant 200 is preferably deployed so that at least a portion of the first bag extends into the lower genital tract, and is preferably removed after use by applying tension to the first bag. If the first bag is formed such that the membrane 280 is secured to itself in multiple places about each of the disks 270, then during withdrawal the disks will slide out of the uterus one by one, permitting them to be withdrawn through a smaller-diameter aperture than if they were withdrawn all together, while the use of two bags protects the uterine wall from shear forces during removal. As discussed above, the membrane can include layers or lubricants.

Figure 3:
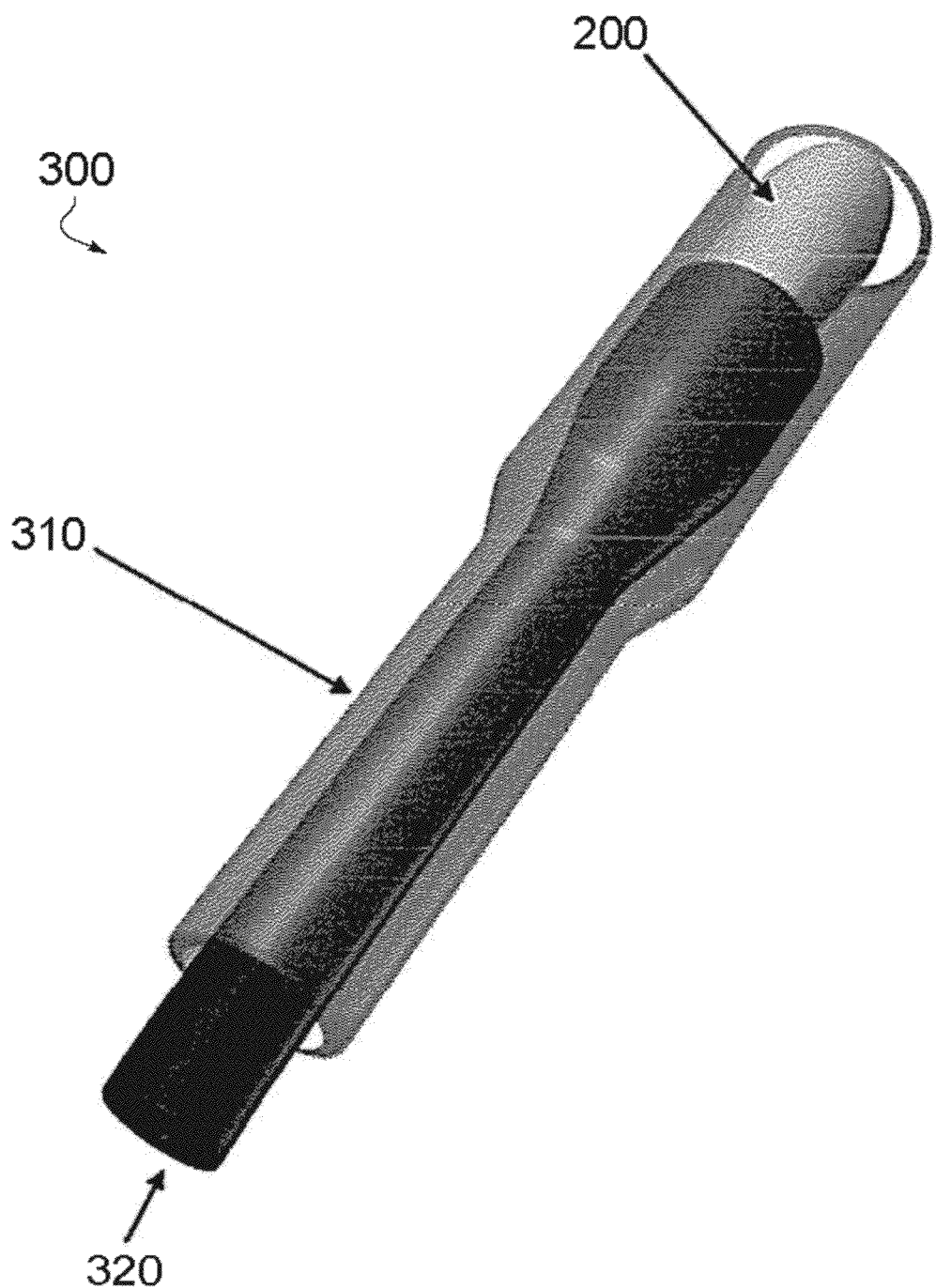
FIG. 3 includes a cross-section of an applicator for a pre-formed implant according to certain embodiments of the invention.
Figure 4:
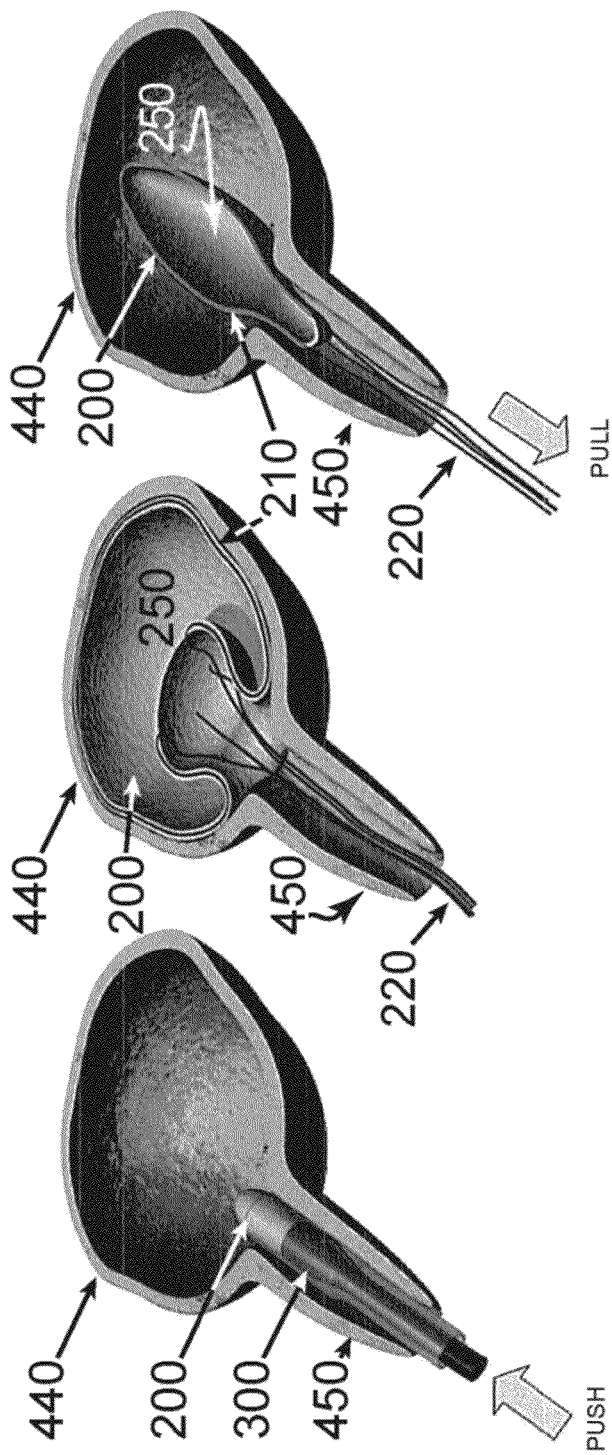
FIG. 4 includes a series of cross sections showing the delivery, use and removal of implants according to certain embodiments of the invention.

Deployment:

In certain embodiments, the implant 200 is delivered with any suitable delivery device or method, such as the applicator 300 as shown in FIG. 3. In one embodiment, the applicator 300 preferably has a roughly cylindrical shape with a length of approximately 14 centimeters, and a diameter of roughly 1.5 cm. In a preferred embodiment, the applicator 300 includes two coaxial cylinders of different diameters. The outer cylinder 310 encloses the implant 200 in a compressed form and an inner cylinder 320 that is slidable within the outer cylinder 310. As shown in FIG. 4, when the applicator 300 is positioned so that the end of the outer cylinder 310 holding the compressed implant 200 is proximate to or has passed through the cervix, the inner cylinder 320 is advanced through the outer cylinder 310, discharging the implant 200 into the uterus where it expands to fit snugly within and apply pressure to the inner uterine wall as discussed above. The applicator 300 is then pulled away, revealing the pull strings 220.

The applicator 300 is depicted in FIG. 3 as straight, but in certain embodiments it is curved and/or includes both rigid and flexible segments that allow it to curve so as to conform to the natural curvature of the lower genital tract as it is inserted and to improve the ease with which it is inserted. In certain embodiments, the inner cylinder 320 advances within the outer cylinder 310 by means of a screw mechanism. The screw mechanism facilitates slow, incremental delivery of an implant to the uterine cavity. Alternatively, the applicator 300 can include a spring-loaded element for retaining and/or discharging the implant. In one embodiment, the spring-loaded element is actuated with a push-button, permitting release of the compressed implant 200 into the uterus with a single button-push for ease of use. In some embodiments, such as the one shown in FIG. 10, the compressed implant 200 is secured within the applicator 300 by one or more deformable elements 320 such as hooks or tabs or a perforated wall to prevent accidental deployment outside of the intended uterine location. The deformable elements are optionally secured to the implant 200 for example at the ends of the pull strings 220 or loops that are integral to the foam or are added during manufacturing such as molding or machining. The deformable elements deform to permit discharge of the implant 200 in response to the application of a force, which can be exerted for example by a portion of the applicator 300 such as a switch, lever or string, or by the implant itself as it is ejected from the applicator. Finally, in some embodiments, the inner cylinder 320 can be manually pushed through the outer cylinder 310 to deploy the implant 200.

In some embodiments, the applicator 300 includes one or more features to improve usability and/or comfort (of either or both of a patient and a user). These may include, as non-limiting examples, a handle or grip, an atruamatic tip, a curved or angled form to permit easier navigation through the lower genital tract and cervix, and the like.

The applicator 300, in certain preferred embodiments, has a diameter of about 3 centimeters and a length of 16-22 inches, or an otherwise suitable length that permits a user to simultaneously (i) maintain a sufficiently firm grip on the applicator 300 and (ii) to insert of a tip of the applicator 300 into or through the lower genital tract and/or the cervix of a patient or, if necessary, into the uterus of a patient where the implant 200 will be deployed.

With respect to handles and grips, in some embodiments, an end of the applicator 300 includes a rough and/or grippable surface. The grippable end in such embodiments preferably has a length of 10-20 centimeters, or otherwise matches a width of a typical user's hand. Handles and grips are formed by any suitable method, including (without limitation) etching the surface of the applicator 300, dipping an end of a portion of the applicator 300 such as an outer cylinder 310 in a handle material such as a silicone rubber, latex, polyurethane, etc., or by bonding or overmolding a handle material to the applicator. The grip or handle may include a flange to further improve a user's grip, may be shaped in an ergonomic fashion, etc. An exemplary applicator 300 including a grip portion is shown in FIG. 16.

Figure 15:
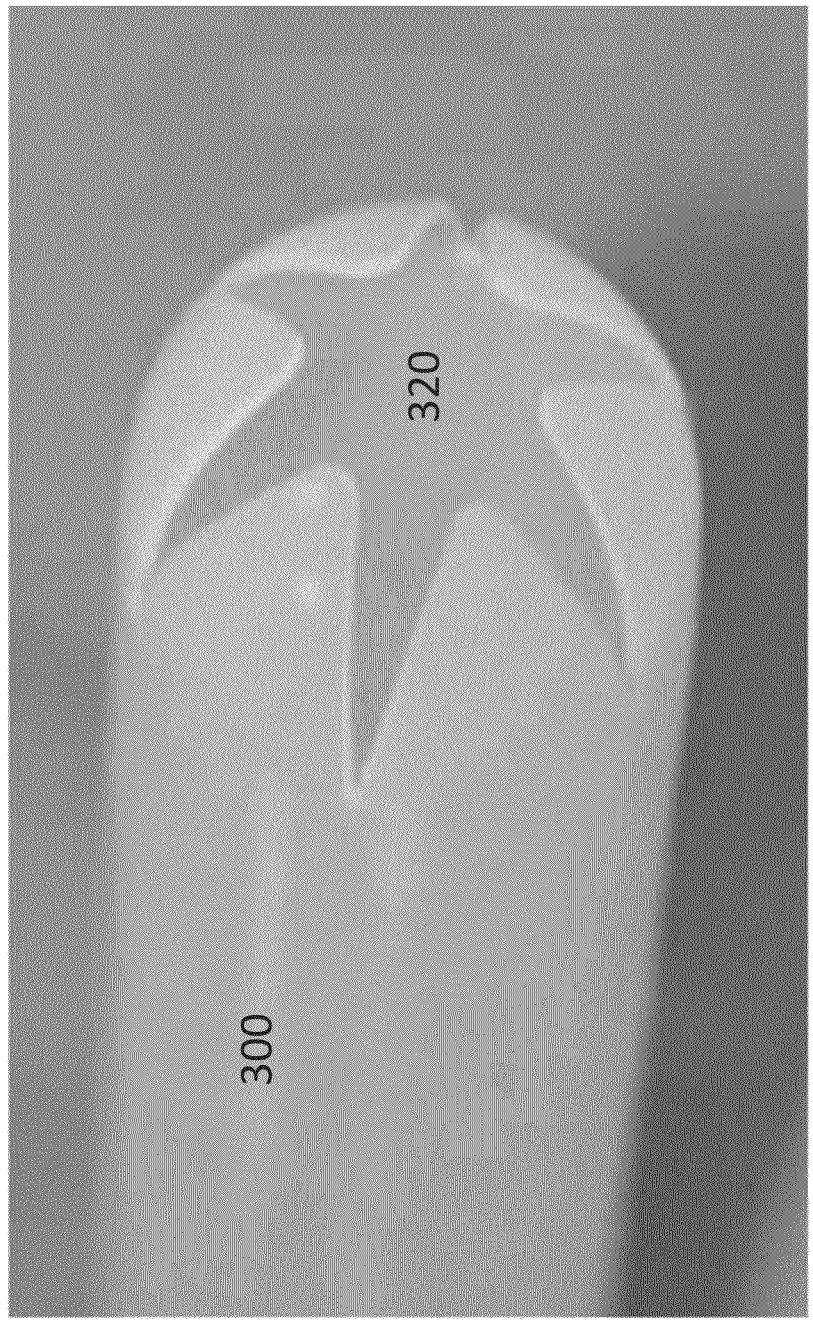
FIG. 15 includes a photo illustration of a delivery device according to certain embodiments of the invention.

With respect to applicator tips, in some embodiments the applicator 300 includes an atraumatic tip, which preferably includes a star- or petal-shaped aperture such as the one shown in FIG. 15. In use, the edges of the tip of the applicator 300 secure the implant 200 and prevent it from being pushed backward into the applicator 300, but can flare outward when the implant 200 is pushed forward through the tip, permitting it to be ejected smoothly from the applicator 300. The outer diameter of the atraumatic tip may include additional features to ease its insertion into and/or through the cervix, such as a lubricious exterior surface or coating, or a narrower outer diameter than other portions of the applicator 300. In some embodiments, the edges of the tip forming the aperture are beveled or rounded to decrease the likelihood of cutting or pinching during insertion. The tip may also have a wall thickness that is thinner and/or softer than the remainder of the portion of the applicator 300 to which it is connected—e.g. the outer cylinder 310. For example, in some embodiments, the outer cylinder 310 has a tapering wall thickness, thicker away from the atraumatic tip, and thinner nearer the aperture. In some embodiments, the atraumatic tip includes a material different than that of the rest of the applicator 300, for example a lower-durometer material may be overmolded or otherwise connected to a higher durometer material forming another portion of the applicator such as the outer cylinder 310. In some embodiments, an end of the implant 200 extends beyond the tip of the applicator 300 as is shown in FIG. 16B. The portion of the implant 200 that extends beyond the applicator 300 optionally includes an atruamatic features or features: as a non-limiting example, the implant 200 may include a ball or other structure that forms as an atruamatic tip when the implant 200 is positioned in the applicator 300, which ball or other structure remains a part of the implant or remains tethered to the implant when it is deployed. Alternatively, the implant 200 may itself form a rounded or ball-like structure when positioned within the applicator 300.

The applicator may be designed to permit loading of a foam implant into an applicator by a user. In some embodiments, the applicator includes a large diameter chamber opposite the tip to hold a foam implant in a fully or partially compressed state prior to deployment. The shaft necks down or forms a funnel as the applicator transitions from the larger diameter chamber to the length designed for insertion. The diameter of this larger section may be up to several times larger than the shaft designed for insertion which limits the strain placed on the foam implant after loading or during storage. Some foams may take a longer time to recover their expanded dimension if kept in a highly compressed state. In another embodiment, there is simply a funnel or tapered portion on the end of the applicator away from the tip. The length of this funnel may be 2 to 20 centimeters and the diameter may increase from the portion designed for insertion by up to several fold. The user will load the foam implant into the applicator using this funneled portion near the time when the patient will be treated. This can be accomplished by holding the foam implant against the funnel and pushing from the opposite end with the pusher rod provided to deploy the implant.

The foam implant 200 optionally includes one or more polymeric or metallic shape memory materials and is fabricated in roughly the conformation that is desired when the implant 200 is deployed in a uterus. Suitable shape memory materials include, without limitation, 83:17 PLA/PCL or 70:30 PLA/PTMC random polymers and cold-hibernated elastic memory polyurethanes as described by Witold Sokolowski, *Shape Memory Polymer Foams For Biomedical Devices,* 2 Open Med. Devices J., 20-23 (2010), the entire disclosure of which is incorporated by reference herein. Generally, suitable shape memory materials will have a crystalline melting temperature above 50° C. and a glass transition temperature between room temperature and body temperature, though any suitable shape memory material is compatible with the invention.

The implant 200 can be collapsed to fit within the applicator 300. When the implant 200 is discharged from the applicator 300, the inclusion of shape memory materials facilitate resumption by the implant 200 of its desired deployed shape. In preferred embodiments, the foam has a glass transition temperature between room temperature (25° C.) and body temperature (37° C.). In an exemplary embodiment the foam implant 200 is fabricated at a temperature above 37° C., then compressed into a conformation for delivery in an applicator 300 and cooled below its glass transition point, preferably to room temperature. When the implant 200 is discharged into a uterus, the shape memory material will be heated above its glass transition point and will drive expansion of the implant 200 into its as-formed configuration, facilitating contact with and the application of pressure to the inner uterine wall.

In some embodiments, the foam implant 200 has a composition such that it collapses and shrinks following curing, but expands when deployed within a uterus and brought into contact with uterine fluids including hemorrhaged blood. Generally, suitable compositions include those produced from high exotherm foaming formulations, though any composition that is otherwise compatible with the invention can be used. In some embodiments, the foam implant 200 includes a hydrogel that is compact when dry, but which absorbs water and expands.

Foam implants of the invention are optionally highly resilient, for example due to a high cross-link density in the polymer comprising the foam, which permits the implants to remain compressed for prolonged periods without losing the ability to resume their cast shape when deployed. The foam implants 200 are optionally compressed by vacuum compression to fit within the applicator 300, and are optionally held in place with a water permeable membrane that disintegrates when it contacts moisture in the uterus.

In certain embodiments, the foam wall 210 has two layers having different properties. The outer layer of the foam wall 210 has superior hemostatic properties and a high degree of softness or compliance to reduce injury to the uterine wall with which it comes in contact. The inner layer of the foam wall 210 has a higher CFD value and provides mechanical support to preserve apposition with the uterine wall. Embodiments involving multiple layers can be useful if a foam having superior hemostatic properties does not have optimal mechanical properties.

In some embodiments, the foam wall 210 is made of polymers with long elongation to break and high crystallinity and low Tg. The implant 200 is shaped so that an elongated neck portion extends through the lower genital tract and, optionally, outside of the patient's body. To remove the implant, a user simply grasps the elongated neck portion and pulls. Because of the long elongation to break, the foam will remain intact during extraction.

The implant 200 can also be made of a material that is solid at the time of deployment, but that dissolves over a period of hours or days, for example PTMC, PLGA and other copolymers with PEG and PPG with different degrees of branching ($2 \leq n \leq 6$). Formulations can include water soluble polymers other than PEG such as PVA as well, such as PEG/PPG copolymers, glycosaminoglycans and/or other polysaccharides, albumin, gelatin or other protein-containing formulations, polyvinylpyrrolidone and polyvinyl alcohol or other suitable water soluble polymers. Alternatively, the foam can be dissolved or decomposed by administering another agent (e.g. vinegar).

Figure 5:
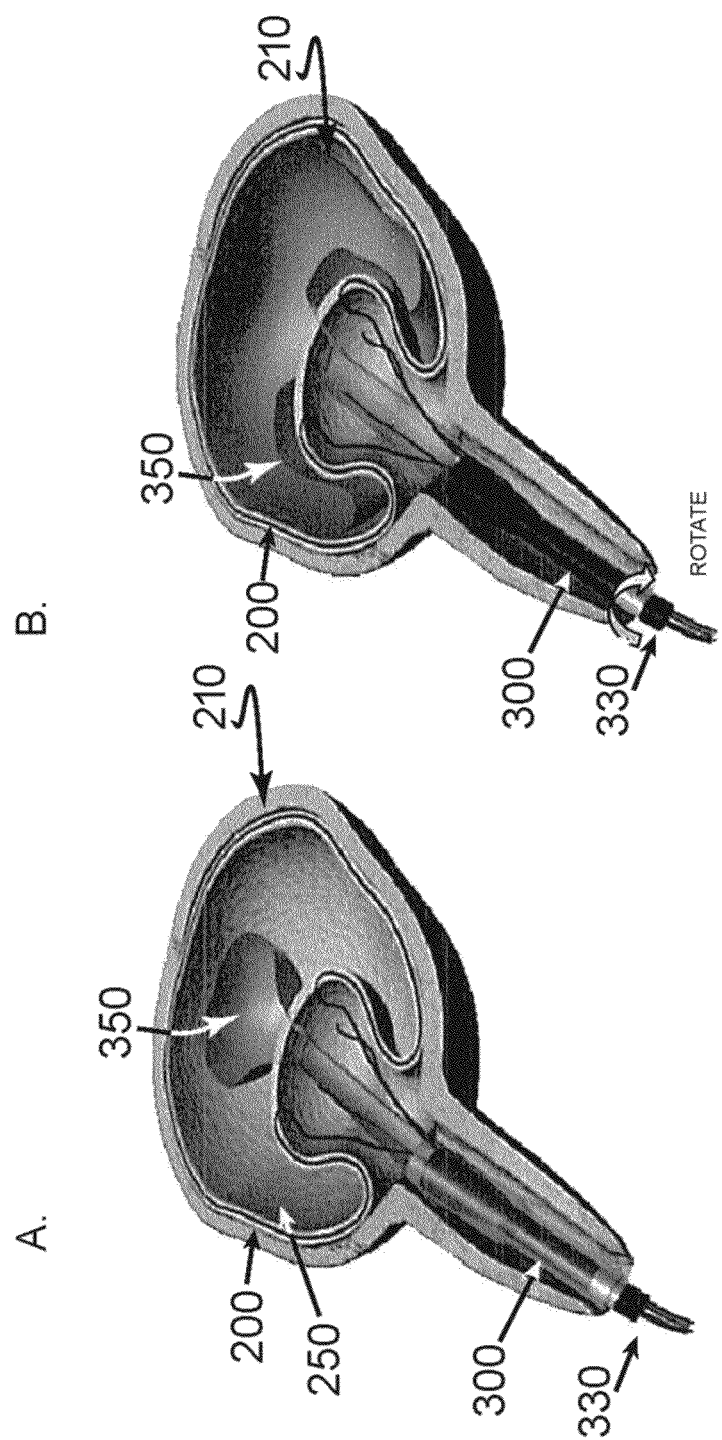
FIG. 5 includes a series of cross sections showing the delivery, use and removal of implants according to certain embodiments of the invention.
Figure 6:
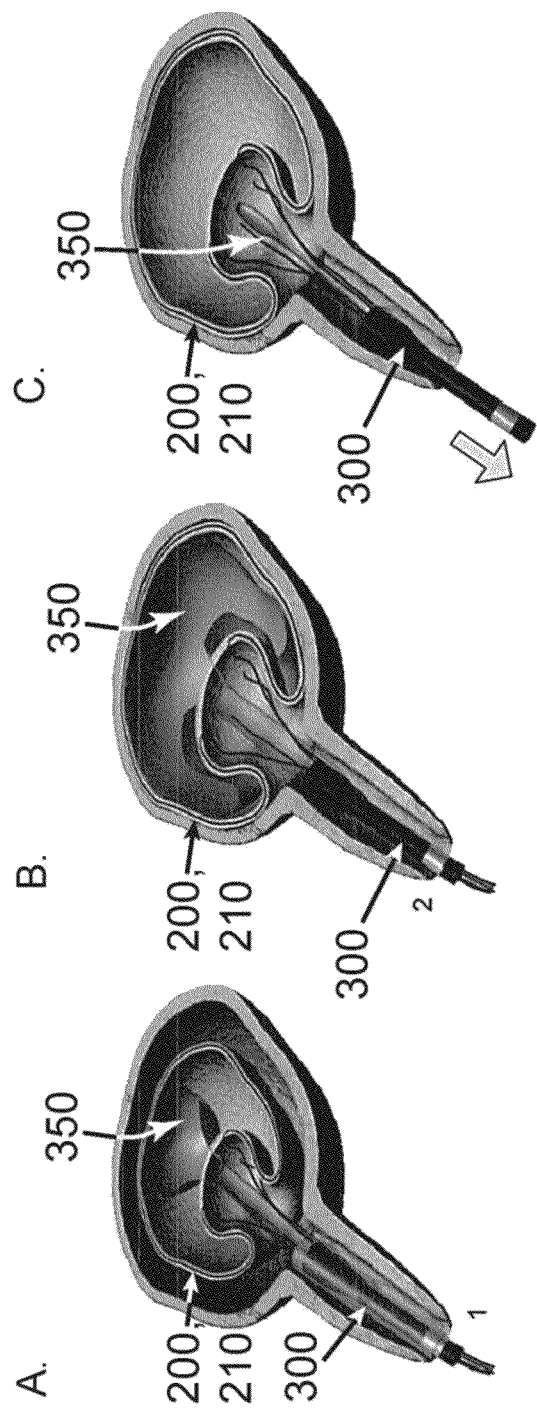
FIG. 6 includes a series of cross sections showing the delivery, use and removal of implants according to certain embodiments of the invention.

Balloon-Aided Expansion:

In certain embodiments, such as the one shown in FIG. 5, the invention is a system for treating uterine hemorrhage including an applicator, 300, and an implant 200 which includes a balloon 350. The end of the balloon 350 is sized to fit within the hollow space 250 of the implant 200. During delivery of the implant 200, the balloon 350 is optionally inflated to promote expansion of the implant 200 so that the wall 210 of the implant 200 makes contact with the uterine wall. The balloon 350 can be inflated for the full duration of use of implant 200, or it can be deflated and periodically re-inflated as necessary to stop further hemorrhage or to further assist in foam expansion. Alternatively, as shown in FIG. 6, the balloon 350 is inflated to facilitate expansion of the implant 200, then deflated and removed while the implant 200 remains in place. In the embodiment depicted in FIG. 5B, after the implant 200 is in place and the balloon 350 is inflated to a suitable size to achieve a desired expansion of the implant 200 and the application of a desired degree of force by the foam wall 210 to the uterine wall, it can be locked in place by, for example, twisting a portion of the applicator 330 to lock the balloon 350 and the pull string or strings 220 in place. When removal of the implant 200 is desired, the applicator 300 is twisted back to facilitate deflation of the balloon 350.

In some embodiments, a balloon catheter 350, such as a Rusch or Foley catheter can be inserted within the hollow space 250 to promote full expansion of the implant 200. The balloon catheter 350 may be left in place while the implant 200 is deployed, or withdrawn, leaving the implant 200 in place as discussed above. A catheter may also be used while the implant 200 is deployed to provide materials to or withdraw materials from the uterus.

In certain embodiments, an airtight membrane is adhered to or embedded beneath or within the foam wall 210, such that the entire implant is inflatable and deflatable.

Figure 7:
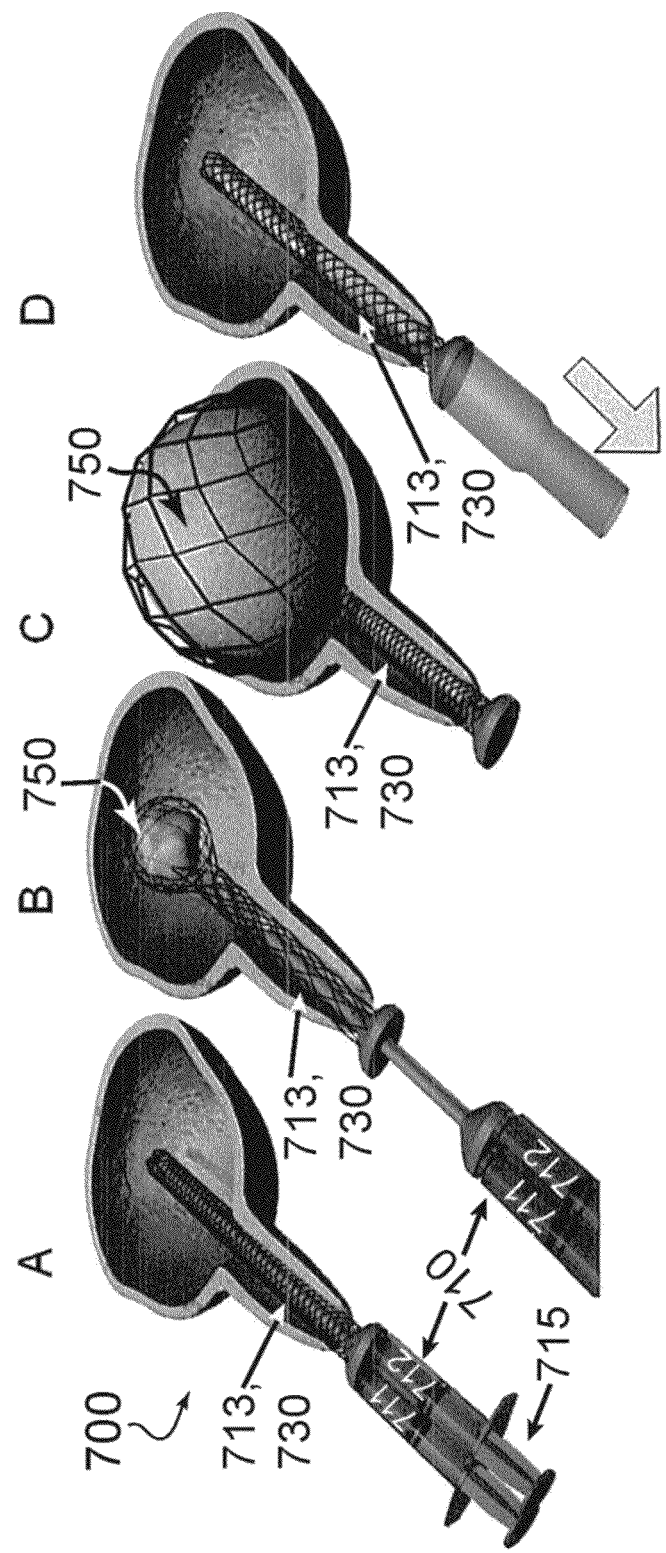
FIG. 7 includes a series of cross sections showing the delivery, use and removal of implants according to certain embodiments of the invention.

The In Situ Forming Implant:

In some embodiments, illustrated in FIG. 7, the invention is a system 700 for forming an implant in situ as described in U.S. patent application Ser. No. 12/862,362. The system 700 includes a two-part applicator 710 having two chambers 711, 712 containing the unmixed two-part formulation in the liquid phase, an applicator tip 713 and a mixing element 714. The applicator tip 713 is optionally covered with a flexible mesh 730 made of polymeric fibers or of Nitinol which can facilitate withdrawal of the implant 200 after use in a manner analogous to the pull strings 220 discussed above. To form the implant, the applicator tip 713 in inserted through the lower genital tract into the uterus. When the plunger 715 of the two-part applicator 710 is depressed, the liquids in the applicator are mixed with air and with each other, and a foam 750 is formed at the applicator tip 713, which foam 750 is enclosed by the mesh 730. The initial volume of the liquid components of the foam is, in certain embodiments, between 5 and 40 mL. This fluid volume expands 25- to 100-fold yielding an implant with a volume of 500-1000 mL. Preferably, the liquid components have a viscosity ranging between 1 and 2000 cP, more preferably between 50-500 cP in order to allow the formulation to be easily dispensed. The dispensing time is preferably less than approximately one minute, more preferably between 1 and 10 seconds in order to stop emergent postpartum hemorrhage quickly. The cream time—the time between mixing and the appearance of small, fine bubbles—is in the range of 5 to 60 seconds, preferably 20 to 40 seconds so that the foam formulation has sufficient time to be dispensed within the uterus before foaming. When deployed, the formulation begins to foam around the mesh 730, pressing both the foam and a portion of the mesh into contact with the uterine wall, while another portion of the mesh 730 is anchored to the applicator tip 713, forming a neck that remains within the lower genital tract. When it is time to remove the foam 750, the application of tension to the neck portion of the mesh 730 compresses the foam 750 back to its original liquid volume, facilitating easy removal.

Figure 8:
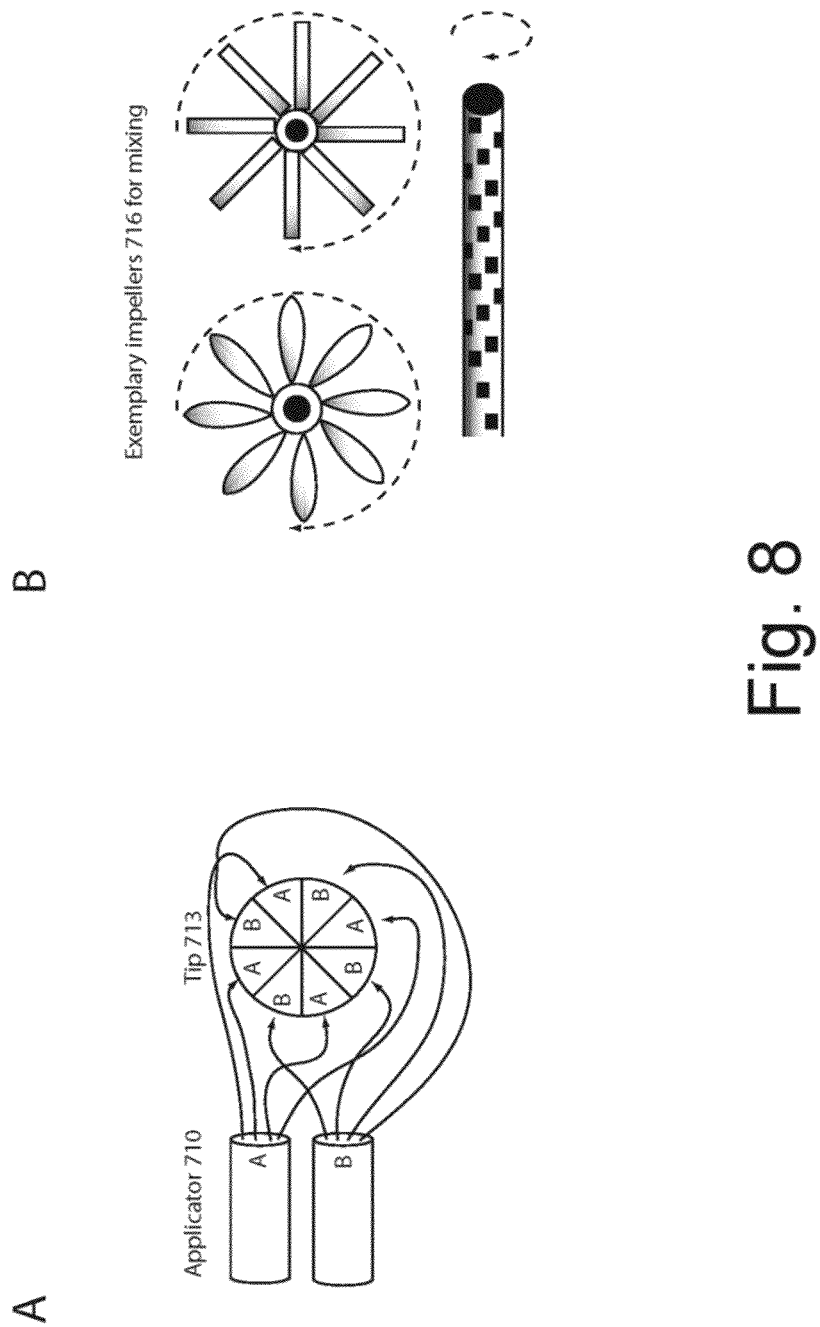
FIG. 8 includes a series of schematic drawings of applicator tips for in situ forming foams according to certain embodiments of the invention.

In these embodiments, the mixing of the introduction of air to the liquid components within the two-part applicator 710 is accomplished via any suitable mechanism known in the art, including directing the flow of the liquid components through a plurality of interdigitated channels as shown in FIG. 8A, so that the area of mixing of the liquid components is maximized relative to the volume of the reagents when they emerge from the applicator tip 713. In certain embodiments, the applicator tip includes an impeller 716 for mixing the liquid components and, optionally, adding air to the mixture. The impeller 716 is propeller shaped in certain embodiments, and is a hollow tube having windows in the wall of the tube in some embodiments; in these embodiments, the impeller rotates to facilitate mixing, as is shown in FIG. 8. The impeller can be powered by an external power source, e.g. a battery, or can be manually powered, e.g. by compression of the plunger of the two-part applicator 710, or by any other suitable means known in the art.

In certain embodiments, low viscosity formulations may be mixed within an applicator 710 by squeezing and/or shaking. In these embodiments, the formulations preferably form a self-propelling foam, so that the mixed formulations can be discharged through the applicator tip 713 without further aeration into a uterus or a bag, as discussed more fully below.

In some embodiments, the delivery system 700 includes a bag 760 positioned so that the fully formed implant 200 is enclosed by a membrane 280 as discussed above. During deployment, mixed and aerated (or self-propelling) formulations may be discharged from the applicator tip 710 into a bag 760 formed by the membrane, which is optionally inside or outside of (or attached to) a flexible mesh 730. The mixture will then foam, expand, and harden into an implant that conforms the uterine wall. In some embodiments, the bag is positioned on the applicator tip 713, which is preferably in fluid communication with, but physically separated from, a mixing chamber 770 into which the formulations in the two chambers are discharged and mixed by the impeller 716 or by shaking and squeezing as discussed above. Physical separation of the bag 760 from the mixing chamber 770 prevents the motion of the impeller 716 from damaging or tearing the bag 760.

As discussed above, the membrane 280 is preferably biocompatible and optionally biodegradable or bioresorbable. The membrane 280 is also preferably semipermeable to permit water and/or other items such as proteins to cross the membrane and enter the foam from the uterus, while fully containing the foam as it is formed and thereafter. If the membrane 280 is fully permeable, it may permit leakage of the formulation and/or the foam as it is created, while if the membrane 280 is impermeable, it will simply act as a balloon and prevent any interaction between the foam and the uterine wall. The membrane 280 may be made of any useful material or materials, including without limitation nylon cloth, and may be textured or smooth, etc., all as described above.

Removal or Decomposition:

Implants of the invention may be removed from the uterus after deployment using any suitable surgical or non-surgical means, including with forceps or hysteroscopically. Implants of the invention may also incorporate features to facilitate removal or decomposition. For example, the implant 200 may be removed through the lower genital tract by pulling on the pull strings 220. As discussed above, the pull strings 220 may be incorporated into the membrane 280 or the foam implant 200 directly, or may be anchored to one or both of the membrane 280 and the implant 200 with securement members.

To facilitate easy withdrawal, the pull strings 220 may be advantageously placed to maximize compression of the implant 200 when tension is applied to the pull strings 220. In certain embodiments, such as the one shown in FIG. 11A, two or more pull strings can be looped around an implant, crossing at one or more points, so that when tension is applied to the free ends of the pull strings 220, pressure is applied about multiple axes of the implant 200, improving stability and providing a high degree of compression during withdrawal. The pull strings 220 are optionally secured to one-another where they cross, for example with a knot or through the use of an external securement member.

With specific reference to the embodiment of FIG. 11A and like embodiments, the implant is, in certain embodiments, foldable along three or more folds, and preferably contains a hollow center. In these embodiments, when the implant is inserted into an applicator, it is inserted in a folded and compressed configuration. Upon deployment, the implant undergoes equal radial expansion, which assists in the establishment of conformal contact with the uterine wall. When tension is applied to the pull strings 220, the process of expansion is essentially reversed: the implant undergoes equal radial compression, facilitating its removal through the lower genital tract.

In certain embodiments, the pull strings may be secured to the outer wall 210 of the foam implant 200 and/or the reinforcing member 230 and/or the membrane 280 by threading through the material, or by one or more securement features such as O-rings, as discussed above. Pull strings 220 may pass through one or more O-rings, promoting the application of tension and/or compressive force at specific sites or along specific axes of the implant 200.

In some embodiments, one or more pull strings 220 are threaded in purse-string arrangements to bring portions of the outer wall 210 of the implant 200 into close apposition with one another, facilitating passage through the lower genital tract.

In embodiments utilizing one or more disks, the purse string or crossed pull string arrangements discussed above may be used, or a plurality of pull strings 220 may be secured to the periphery of the disk and/or to a portion of a membrane 280 covering the periphery of the disk, and threaded through a hole in the central portion of the disk, again promoting a high degree of compression and stability when tension is applied to the pull strings 220.

After use, coagulated blood may accumulate in the implant 200, hindering compression and withdrawal of the implant 200 through the lower genital tract. In some embodiments, implants of the invention can be withdrawn as separate small pieces having a smaller profile than the implants as a whole. Implants can include perforations or other regions of weakness that allow the implant to be torn or sheared into separate pieces and/or may comprise separately formed pieces that are weakly held together by adhesive, sutures, or other suitable means that can be easily separated. Integrated or separate structures can be compressed into the delivery system and deployed as a whole, while separate structures may also be deployed separately. At time of removal, pieces of the implant, preferably with a substantially lower profile than the implant as a whole, can be removed individually and sequentially, facilitating removal through lower genital tract, particularly when the foam has accumulated material during uses and becomes more difficult to compress for retrieval.

EXAMPLES

Certain principles and embodiments of the invention are illustrated by the following non-limiting examples:

Example 1

Stacked Disk Design

The foam used in implants according to this embodiment is a two-part polyol-isocyanate formulation.

Foams for implants of the invention are created in large blocks by combining a polyol mixture with an isocyanate. The foam blocks are machined into disks using an electric knife (Hamilton Beach, Southern Pines, N.C.), though any suitable shaping means known in the art may be used. For the lead stacked disk design, the blocks are cut into slices 3 cm thick with diameters ranging between 5 and 15 cm. The edge of one face is cut diagonally along the circumference to create a disc thickest at the center, and tapered toward the edges. Five stacked disks comprise the foam implant.

Example 2

Removal System

Figure 17:
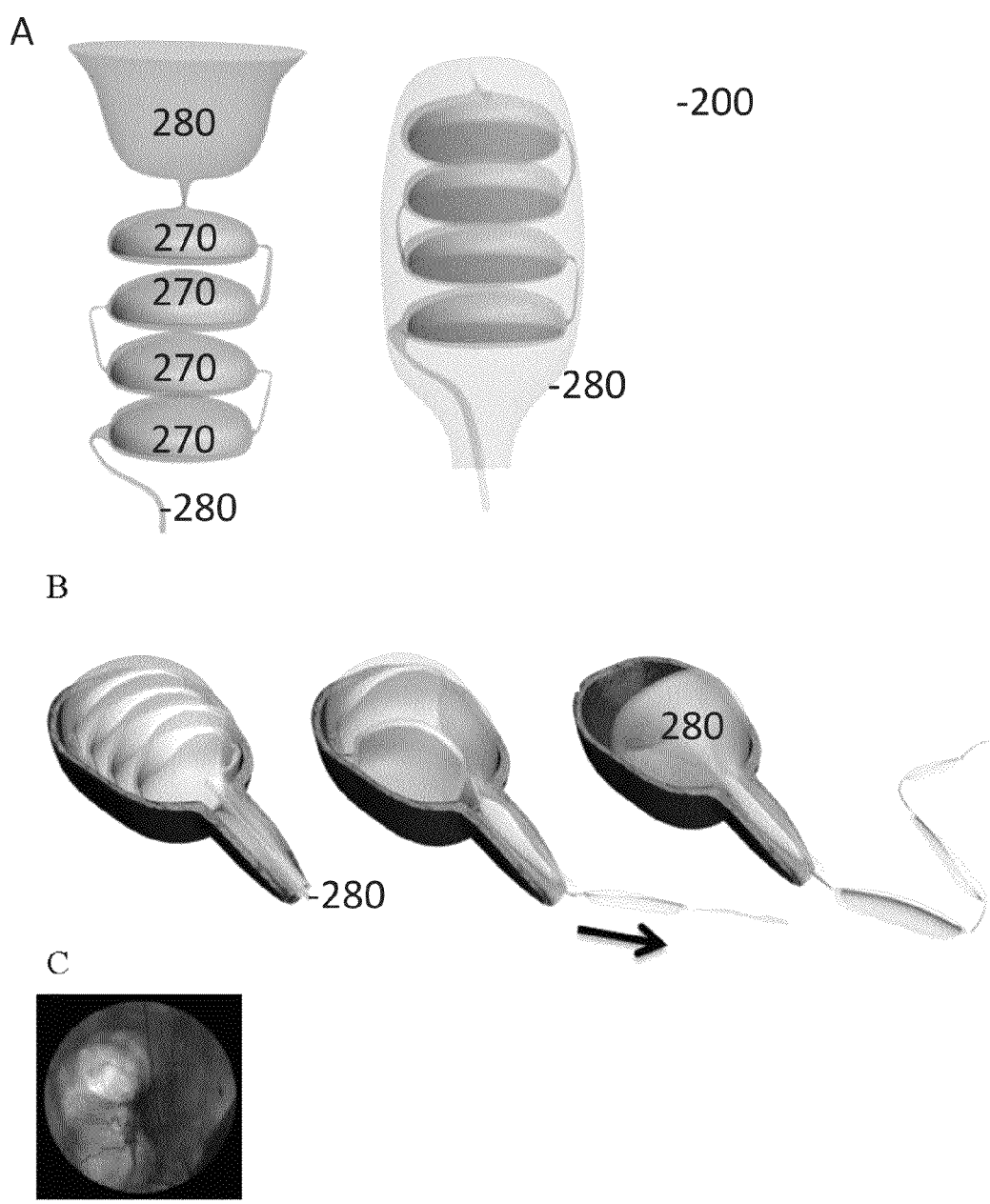
FIG. 17 includes schematic views of implants and angiographic views of deployed implants according to embodiments of the invention.

All foams are contained in a two-layer, low friction, porous bag made of nylon fabric (PBN-II 0.50 osy, Cerex Advanced Fabrics, Cantonment Fla.). The inner layer (also referred to as the inner bag) covers each individual disk and the outer layer encases the entire stack of disks. The inner and outer bags are attached to each other at the distal end of the stack. The inner bag is manufactured by placing the disks 5 cm apart in a row on a rectangular piece of nylon fabric. The fabric is folded in half over the disks. A sewing machine (Brother, Bridgewater N.J.) is used to sew a seam around each disk. The fabric between each disk is twisted into a rope and sewn in place, resulting in a string of disks. The string of disks are stacked on top of each other accordion style. The outer bag is pulled over the stacked disks, as shown in FIG. 17A.

Only the outer bag is in contact with the vaginal canal, cervix and uterus. An extension of the inner bag extends outside the patient and is within reach of the user. To remove the implant, as illustrated in FIG. 17B, the user pulls firmly on the extension, and the disks slide out sequentially. Inside the uterus, the disks are sliding against the stationary outer bag instead of against the tissues. This design eliminates abrasion along the patient's tissues as the implant is removed. Since the bags are attached to each other at the distal end, the outer bag is removed after the disks in one continuous pulling motion.

This single pulling action turns the outer bag inside-out as it is gently peeled away from the uterine cavity, which is expected to minimize disruption of blood clots.

Example 3

Attenuation of Flows in a Benchtop Model

A silicone benchtop uterine model was created that mimics the size and anatomy of a postpartum uterus. The semi-transparent model permits evaluation of the expansion and conformal contact of the foam to the uterine walls. A silicone vessel which models the compliance of a human uterine artery runs along the length of the uterine model. The compliant silicone vessel is connected to a static fluid pressure head to create physiologically relevant blood flow and pressure through the vessel. This setup allows us to assess the foam prototypes' ability to exert pressure on the uterine walls and impact flow in the uterine artery.

Foam prototypes oversized 25%, 50%, and 75% to the uterine width were tested in the uterine model and compared to the Bakri Postpartum Balloon (Cook Medical Incorporated, Bloomington Ind.), the control device. The foam prototypes were loaded into the delivery applicator, deployed into the model, and removed by the pull membrane. The Bakri balloon was inserted into the model and filled with 500 mL of saline, injected in a series of 50 mL increments. The balloon was removed by draining the saline and pulling the balloon out. The balloon procedure was performed in accordance with the instructions for use provided with the product. All foam test devices, as well as the balloon, demonstrated flow stoppage in the silicone model.

Example 4

Evaluation of Withdrawal Force

The force required to remove disks from the uterus was measured with an Instron mechanical test system (Norwood, Mass.). The silicone uterine model was secured to the base and foam disks were deployed into the model with the delivery applicator. The inner membrane that remained outside of the uterine model opening external to the model was clamped to the test fixture. The test fixture was programmed to pull upward at a constant rate until all of the disks were removed and to measure the tensile force applied. For disks oversized 19-76% to the uterine model, the tensile force recorded to remove the disks was between 3.2 pound-feet (lbf) and 11.2 lbf.

Example 5

In Vivo Deployment of Implants

Implants of the invention were implanted into ewes to i) demonstrate foam deployment from the delivery applicator and removal by pulling on inner bag, ii) observe foam expansion within the uterus and apposition to uterine walls, and iii) evaluate Bakri balloon usage for comparison. During the study, we were able to demonstrate deployment, expansion, and removal of a foam sphere prototype and a Bakri balloon. An incision was made in the abdomen and cervical canal to maneuver the delivery applicator to the uterine opening and bypass the tortuous cervical rings found in sheep. The foam sphere fully deployed and expanded within the right uterine horn (sheep possess two uterine horns separated by a septum). Slight uterine contraction was observed, and the uterine artery was visibly pulsing in an intermittent manner. The foam was removed through the cervical canal by pulling on the inner bag. No tissue trauma or uterine prolapse due to removal was observed. For comparison, the Bakri balloon was also deployed and removed per indication for use. Faster deployment and removal procedure times were recorded for the foam sphere (2:21 deployment; 1:20 removal) than the Bakri balloon (14:12 deployment, 2:27 removal).

Example 5

Reduction of Uterine Artery Flow In Vivo

A second preclinical study was performed to i) demonstrate foam deployment and removal in a closed abdomen ewe, ii) measure reduction in uterine artery flow due to the test device, iii) confirm foam expansion within the uterine horn and apposition to uterine walls, iv) evaluate Bakri balloon for comparison, and v) assess minimum and maximum foam disc sizes with respect to efficacy and safety. This study demonstrated procedural deployment, expansion, and removal success of the lead AM 62 foam disc design in three sizes (25%, 50% and 75% oversize to uterine diameter). The delivery applicator was inserted through the vagina and cervical canal, and the foam fully deployed within the uterine horn. Full expansion and wall apposition was observed via angiogram, as shown in FIG. 17C. Uterine artery flow was visualized via cinefluoroscopy before and after foam deployment. Based on the time for contrast to flow through a specified segment of the uterine artery, flow reduction could be assessed. The 50% oversized discs demonstrated greater flow reduction compared to the Bakri balloon.

FURTHER REMARKS

The invention has been described with an emphasis on treatment of hemorrhage generally, and postpartum hemorrhage in particular. However, those skilled in the art will appreciate that implants, formulations and materials of the invention are adaptable to suit a wide variety of applications, particularly contraception, treatment of genital tract infections, for example by replacing or supplementing portions of the invention disclosed above with agents useful for the selected applications, in particular spermicides, antibiotics, antimycotics, etc. and by modifying the scale of implants, the volume of material or formulation delivered to a patient, the hydrophilicity of the foam implant, etc. to suit the application of interest. The invention is also adaptable to function as an ordinary tampon, subject to modifications along the lines set forth above.

The term "and/or" is used throughout this application to mean a non-exclusive disjunction. For the sake of clarity, the term A and/or B encompasses the alternatives of A alone, B alone, and A and B together. The aspects and embodiments of the invention disclosed above are not mutually exclusive, unless specified otherwise, and can be combined in any way that one skilled in the art might find useful or necessary.

The term "pore" is used throughout the application to refer to chambers within foams of the invention. The term "drug" is used to mean any bioactive agent, including without limitation pharmaceuticals, biomolecules, nucleotides, toxins, and the like, as well as any suitable vector, excipient, adjuvant, salt, solvent, filler, substrate, buffer, filler or formulation necessary or useful to deliver the above to a patient or to obtain an activity before, during or after such delivery.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The breadth and scope of the invention is intended to cover all modifications and variations that come within the scope of the following claims and their equivalents.

What is claimed is:

1. A method of treating uterine hemorrhage, comprising:
   positioning a foam within the uterus of a patient, the foam comprising a plurality of disk-shaped polymer foam bodies and at least one membrane disposed over at least a portion of an exterior surface of the disk-shaped polymer foam bodies;
   wherein the membrane comprises at least one securement feature attaching the membrane to itself or to the foam;
   wherein each disk-shaped foam body includes a central portion and an edge portion, the central portion having a thickness that is greater than a thickness of the edge portion; and
   applying tension to the membrane to sequentially withdraw the disk-shaped polymer foam bodies from the uterus of the patient.

2. The method of claim 1, wherein the foam has a volume of between 100% and 200% of the volume of a postpartum human uterus.

3. The method of claim 1, wherein the at least one polymer foam body is characterized by a compression force deflection value at 50% compression of less than 100 kPa.

4. The method of claim 1, wherein the foam includes a drug that promotes blood clotting.

5. The method of claim 1, wherein the foam is configured to cause a uterine contraction by applying pressure thereto.

6. The method of claim 1, wherein the foam is configured to apply a pressure of at least 30 mmHg to a uterine wall.

7. The method of claim 1, wherein the polymer foam body is formed within a uterus of the patient.

8. The method of claim 1, wherein the biocompatible polymer foam body is pre-formed prior to said step of positioning the foam within the uterus of the patient.

9. The method of claim 1, further comprising the step of compressing said foam into an applicator.

10. The method of claim 1, wherein the at least one securement feature is selected from the group consisting of hooks, rings, sutures, and staples.

* * * * *